(12) United States Patent
Uber, III et al.

(10) Patent No.: US 10,857,345 B2
(45) Date of Patent: *Dec. 8, 2020

(54) STERILITY RETAINING MEDICAL CONNECTOR ASSEMBLY AND METHOD

(71) Applicant: BAYER HEALTHCARE LLC, Whippany, NJ (US)

(72) Inventors: Arthur E. Uber, III, Pittsburgh, PA (US); Kevin Cowan, Allison Park, PA (US); James A. Dedig, Pittsburgh, PA (US); David M. Griffiths, Pittsburgh, PA (US); Edward J. Rhinehart, Murrysville, PA (US); Benjamin Taggart, Cheswick, PA (US); Mark Trocki, Cheswick, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 40 days.

This patent is subject to a terminal disclaimer.

(21) Appl. No.: 15/974,764

(22) Filed: May 9, 2018

(65) Prior Publication Data

US 2018/0256882 A1 Sep. 13, 2018

Related U.S. Application Data

(63) Continuation of application No. 14/352,449, filed as application No. PCT/US2012/060978 on Oct. 19, 2012, now Pat. No. 9,993,636.

(Continued)

(51) Int. Cl.
*A61M 39/16* (2006.01)
*A61M 39/10* (2006.01)
(Continued)

(52) U.S. Cl.
CPC .......... *A61M 39/165* (2013.01); *A61M 39/10* (2013.01); *A61M 39/1011* (2013.01);
(Continued)

(58) Field of Classification Search
CPC .... A61M 39/10; A61M 39/16; A61M 39/165; A61M 39/22; A61M 39/24; A61M 39/26;
(Continued)

(56) References Cited

U.S. PATENT DOCUMENTS

| 2,287,746 A | 6/1942 | Morton |
| 2,731,053 A | 1/1956 | Lockhart |

(Continued)

FOREIGN PATENT DOCUMENTS

| EP | 1331020 A1 | 7/2003 |
| EP | 1834664 B1 | 5/2013 |

(Continued)

OTHER PUBLICATIONS

The International Preliminary Report on Patentability dated Apr. 22, 2014 from corresponding PCT Application No. PCT/US2012/060978 filed Oct. 19, 2012.

(Continued)

*Primary Examiner* — Kami A Bosworth
(74) *Attorney, Agent, or Firm* — David Schramm; Joseph L. Kent; James R. Stevenson

(57) ABSTRACT

A medical connector assembly for establishing a fluid connection between a first medical device and a second medical device includes a multi-use connector and a plurality of single-use connectors connected in series. The multi-use connector has a proximal end opposite a distal end along a longitudinal length thereof. The plurality of single-use connectors each have a proximal end opposite a distal end along a longitudinal length thereof. The distal end of the multi-use connector is releasably connected to the proximal end of a (Continued)

first of the serially-connected single-use connectors. When a second of the serially-connected single-use connectors is disconnected from the first single-use connector, the first single-use connector remains connected to the multi-use medical connector as a sterility retaining cover.

17 Claims, 37 Drawing Sheets

Related U.S. Application Data

(60) Provisional application No. 61/548,862, filed on Oct. 19, 2011.

(51) Int. Cl.
    *A61M 39/18*     (2006.01)
    *A61M 39/20*     (2006.01)
    *F16L 25/00*     (2006.01)
    *A61M 39/26*     (2006.01)

(52) U.S. Cl.
    CPC ............ *A61M 39/18* (2013.01); *A61M 39/20* (2013.01); *F16L 25/00* (2013.01); *A61M 2039/1044* (2013.01); *A61M 2039/1061* (2013.01); *A61M 2039/267* (2013.01); *Y10T 137/8811* (2015.04)

(58) Field of Classification Search
    CPC .. A61M 2039/1011; A61M 2039/1016; A61M 2039/1033; A61M 2039/1038; A61M 2039/1061; A61M 2039/1066; A61M 2039/1072; A61M 2039/1077; A61M 2039/1083; A61M 2039/1088; A61M 2039/2406–2493; A61M 2039/261–268; Y10T 137/8811
    See application file for complete search history.

(56) References Cited

U.S. PATENT DOCUMENTS

| | | |
|---|---|---|
| 2,780,243 A | 2/1957 | Williams et al. |
| 2,798,487 A | 7/1957 | Ferguson |
| 2,938,238 A | 5/1960 | Gewecke et al. |
| 2,997,043 A | 8/1961 | Flynn |
| 3,164,279 A | 1/1965 | Towns |
| 3,480,299 A | 11/1969 | Harold |
| 3,658,061 A | 4/1972 | Hall |
| 3,835,862 A | 9/1974 | Villari |
| 3,916,929 A | 11/1975 | Brown |
| 3,986,508 A | 10/1976 | Barrington |
| 3,987,930 A | 10/1976 | Fuson |
| 4,106,654 A | 8/1978 | Jones |
| 4,187,846 A | 2/1980 | Carminucci et al. |
| 4,194,509 A | 3/1980 | Ferguson et al. |
| 4,230,231 A | 10/1980 | Burnett et al. |
| 4,256,106 A | 3/1981 | Shoor |
| 4,340,148 A | 7/1982 | Beckham |
| 4,360,969 A | 11/1982 | Collier |
| 4,366,816 A | 1/1983 | Bayard et al. |
| 4,398,757 A | 8/1983 | Floyd et al. |
| 4,433,973 A | 2/1984 | Kurtz et al. |
| 4,450,624 A | 5/1984 | Collier |
| 4,511,359 A | 4/1985 | Vaillancourt |
| 4,551,146 A | 11/1985 | Rogers |
| 4,559,043 A | 12/1985 | Whitehouse et al. |
| 4,579,823 A | 4/1986 | Ryder |
| 4,624,664 A | 11/1986 | Peluso et al. |
| 4,636,204 A | 1/1987 | Christopherson et al. |
| 4,775,369 A | 10/1988 | Schwartz |
| 4,778,447 A | 10/1988 | Velde et al. |
| 4,795,426 A | 1/1989 | Jones |
| 4,810,241 A | 3/1989 | Rogers |
| 4,883,641 A | 11/1989 | Wicks et al. |
| 4,950,260 A | 8/1990 | Bonaldo |
| 4,981,469 A | 1/1991 | Whitehouse et al. |
| 5,057,088 A | 10/1991 | Narayanan et al. |
| 5,088,984 A | 2/1992 | Fields |
| 5,098,395 A | 3/1992 | Fields |
| 5,171,229 A | 12/1992 | McNeil et al. |
| 5,184,742 A | 2/1993 | Decaprio et al. |
| 5,221,267 A | 6/1993 | Folden |
| 5,280,809 A | 1/1994 | Tive |
| 5,292,308 A | 3/1994 | Ryan |
| 5,340,359 A | 8/1994 | Segura Badia |
| 5,382,242 A | 1/1995 | Horton et al. |
| 5,413,280 A | 5/1995 | Taylor |
| 5,482,171 A | 1/1996 | Palmer |
| 5,492,147 A | 2/1996 | Challender et al. |
| 5,498,253 A | 3/1996 | Aswad et al. |
| 5,569,181 A | 10/1996 | Heilman et al. |
| 5,620,433 A | 4/1997 | Aswad et al. |
| 5,739,508 A | 4/1998 | Uber, III |
| 5,746,718 A | 5/1998 | Steyn |
| 5,771,935 A | 6/1998 | Myers |
| 5,785,691 A | 7/1998 | Vetter et al. |
| 5,803,510 A | 9/1998 | Dorsey, III et al. |
| 5,806,519 A | 9/1998 | Evans, III et al. |
| 5,840,026 A | 11/1998 | Uber, III et al. |
| 5,843,037 A | 12/1998 | Uber, III |
| 5,853,096 A | 12/1998 | Bartur et al. |
| 5,913,434 A | 6/1999 | Fukuhara et al. |
| 5,972,292 A | 10/1999 | Demeo |
| 6,077,259 A | 6/2000 | Caizza et al. |
| 6,164,279 A | 12/2000 | Tweedle |
| 6,261,270 B1 | 7/2001 | Gault et al. |
| 6,511,472 B1 | 1/2003 | Hayman et al. |
| 6,666,839 B2 | 12/2003 | Utterberg et al. |
| 6,814,726 B1 | 11/2004 | Lauer |
| 6,821,267 B2 | 11/2004 | Veillon et al. |
| 6,911,025 B2 | 6/2005 | Miyahara |
| 7,040,598 B2 | 5/2006 | Raybuck |
| 7,070,589 B2 | 7/2006 | Ebner et al. |
| 7,083,605 B2 | 8/2006 | Miyahara |
| 7,097,209 B2 | 8/2006 | Unger et al. |
| 7,241,285 B1 | 7/2007 | Dikeman |
| 7,374,555 B2 | 5/2008 | Heinz et al. |
| 7,452,349 B2 | 11/2008 | Miyahara et al. |
| 7,731,155 B2 | 6/2010 | Funamura et al. |
| 7,740,288 B2 | 6/2010 | Mantell |
| 7,938,454 B2 | 5/2011 | Buchanan et al. |
| 8,012,144 B2 | 9/2011 | Moberg |
| 9,358,333 B2 | 6/2016 | Trombley, III et al. |
| 9,393,441 B2 | 7/2016 | Hoffman et al. |
| 9,408,971 B2 | 8/2016 | Carlyon et al. |
| 2001/0016704 A1 | 8/2001 | Zadno-Azizi et al. |
| 2002/0010437 A1 | 1/2002 | Lopez et al. |
| 2002/0093192 A1 | 7/2002 | Matkovich |
| 2004/0111078 A1 | 6/2004 | Miyahara |
| 2004/0227120 A1 | 11/2004 | Raybuck |
| 2005/0090805 A1 | 4/2005 | Shaw et al. |
| 2005/0107765 A1 | 5/2005 | Kashmiran et al. |
| 2005/0256460 A1* | 11/2005 | Rome .................... A61M 39/26 604/247 |
| 2008/0071219 A1 | 3/2008 | Rhinehart et al. |
| 2008/0071220 A1 | 3/2008 | Rhinehart et al. |
| 2008/0097342 A1 | 4/2008 | Gordin |
| 2008/0129042 A1* | 6/2008 | Weigel ............... A61M 39/1011 285/92 |
| 2008/0177250 A1 | 7/2008 | Howlett et al. |
| 2009/0102192 A1 | 4/2009 | Ziman |
| 2009/0182309 A1 | 7/2009 | Muffly |
| 2009/0216192 A1 | 8/2009 | Schriver et al. |
| 2010/0049170 A1 | 2/2010 | Solomon et al. |
| 2011/0049866 A1 | 3/2011 | Trombley, III et al. |
| 2011/0054440 A1 | 3/2011 | Lewis |
| 2011/0118612 A1* | 5/2011 | Miller .................. A61B 5/0215 600/486 |
| 2011/0184382 A1 | 7/2011 | Cady |
| 2011/0240158 A1 | 10/2011 | Py |

(56) References Cited

U.S. PATENT DOCUMENTS

2013/0079581 A1   3/2013   Agamaite et al.
2013/0123567 A1   5/2013   Agamaite et al.
2013/0331634 A1  12/2013   Kaintz et al.

FOREIGN PATENT DOCUMENTS

| JP | 2001238945 A | 9/2001 |
| JP | 2003210574 A | 7/2003 |
| JP | 2008528173 A | 7/2008 |
| WO | 9103404 A1 | 3/1991 |

OTHER PUBLICATIONS

The International Search Report and Written Opinion of related PCT Application No. PCT/US2014/044500, dated Nov. 4, 2014.
The International Search Report for corresponding PCT Application No. PCT/US2012/060978, dated Feb. 5, 2013.
The Supplementary European Search Report dated Feb. 16, 2015 from corresponding EP Application No. EP12842335.
Hadaway, Lynn, Needleless Connectors: A Primer on Terminology, Journal of Infusion Nursing, Jan./Feb. 2010, 33(1): 22-31.
"Ultraport Swabbable Port Stopcocks, B. Braun Sharing Expertise.", accessed online on Apr. 14, 2014.

* cited by examiner

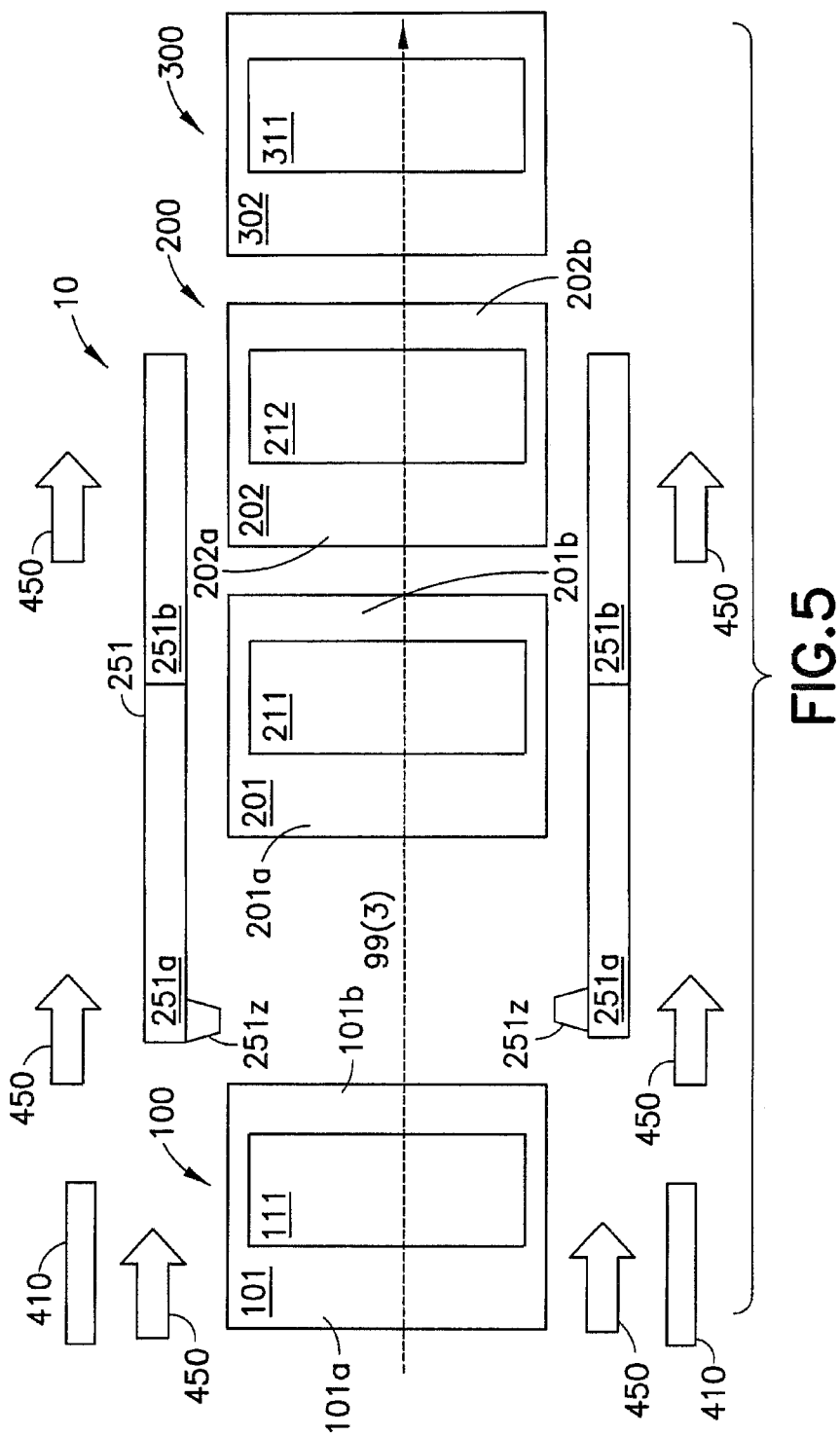

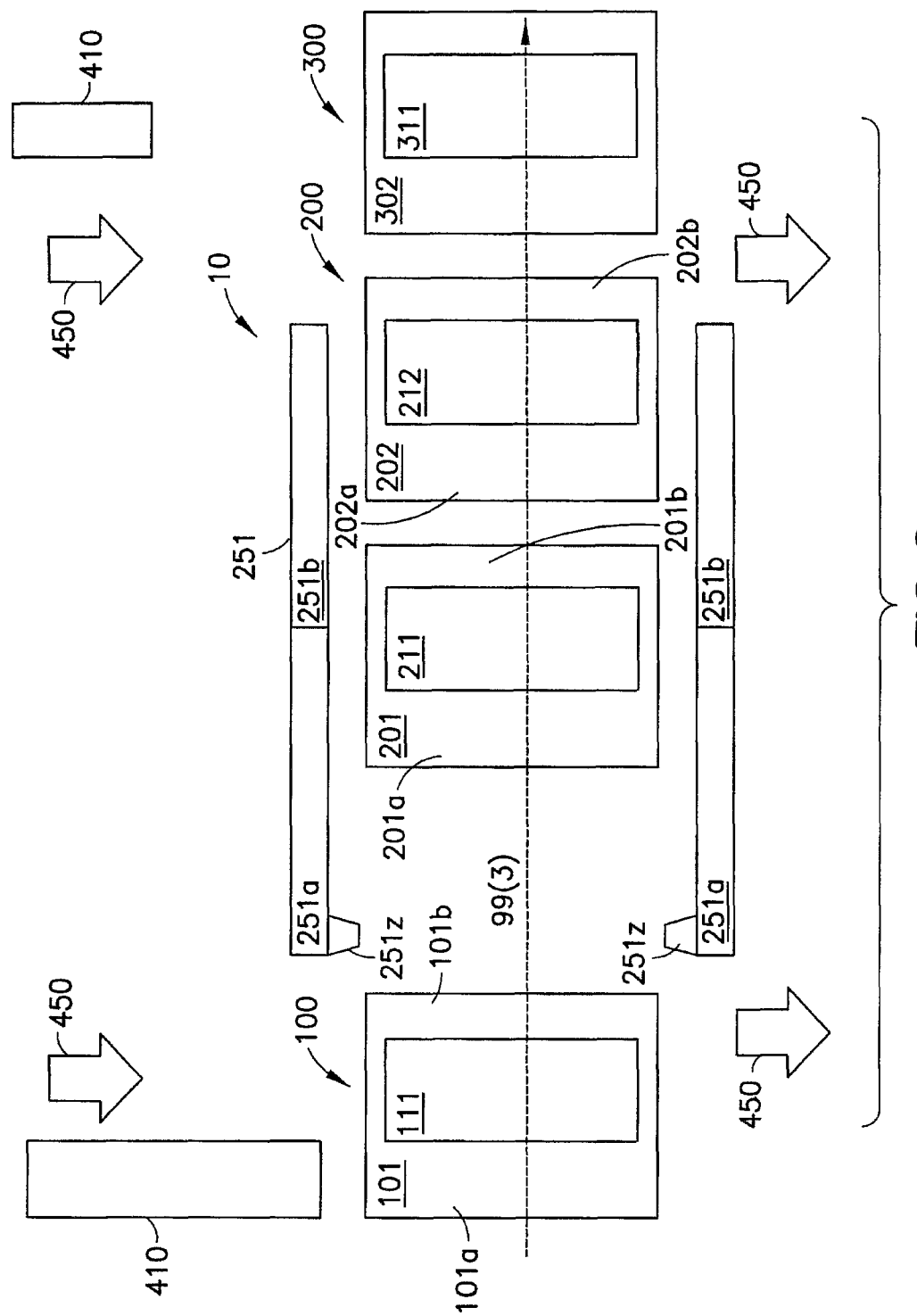

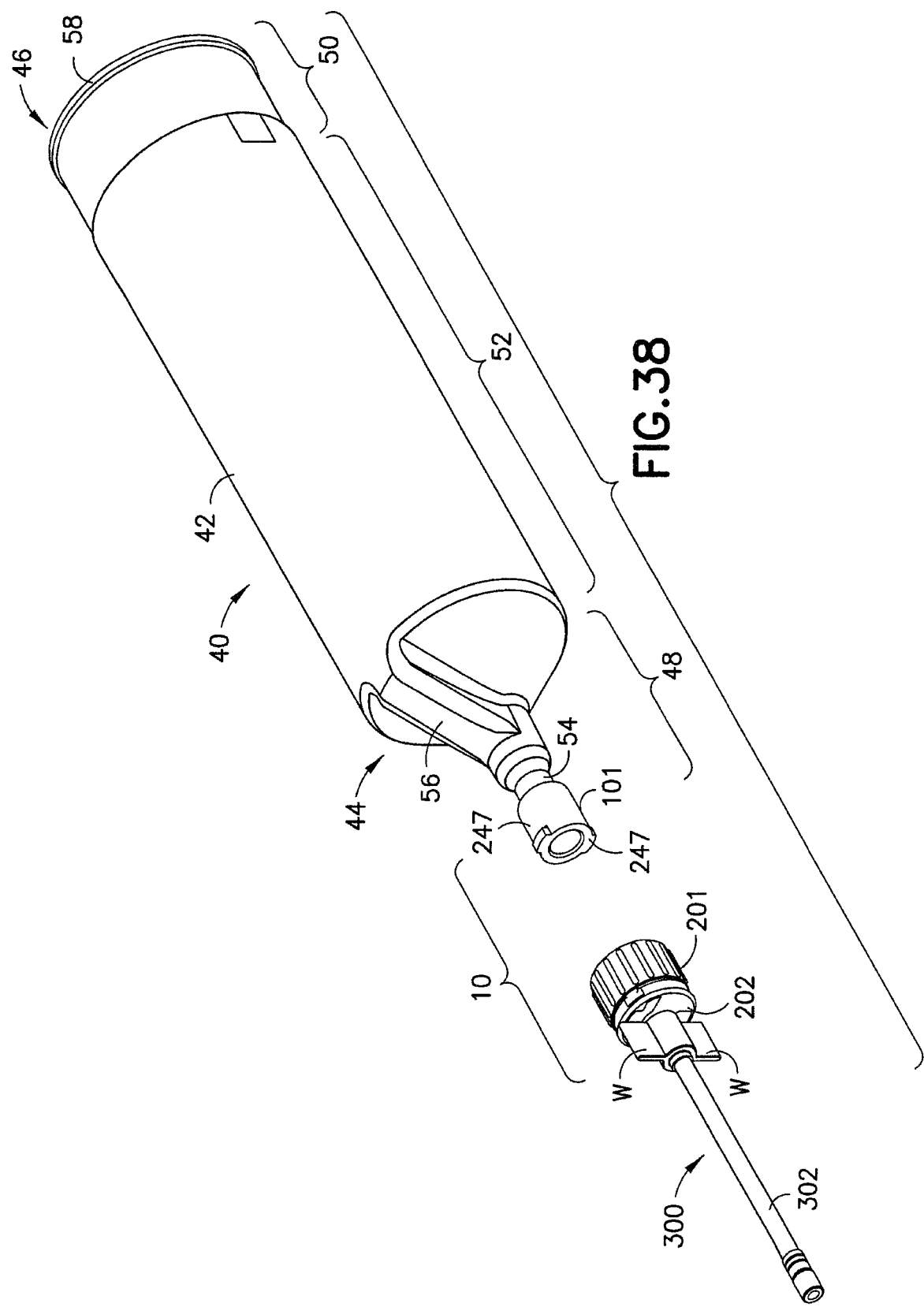

STERILITY RETAINING MEDICAL CONNECTOR ASSEMBLY AND METHOD

CROSS REFERENCE TO RELATED APPLICATION

This Application is a Continuation Application of U.S. Ser. No. 14/352,449, filed Apr. 17, 2014, now issued as U.S. Pat. No. 9,993,636, which is a 371 national phase application of PCT International Application No. PCT/US2012/060978, filed Oct. 19, 2012, and designating the United States of America, which claims the benefit from the earlier filed U.S. Provisional Application No. 61/548,862, filed Oct. 19, 2011, entitled "Sterility Retaining Medical Connector Assembly and Method," and is hereby incorporated into this application by reference as if fully set forth herein.

BACKGROUND OF THE INVENTION

Field of the Invention

This disclosure relates, in general, to the field of medical connectors and, more particularly, to a medical connector assembly for retaining sterility of a reusable portion of the medical connector assembly.

Description of the Related Art

Typical medical connectors are provided for use with various medical devices, including dosage containers, administration sets, catheters, and medical lines. These connectors are commonly used in numerous medical procedures where it is necessary to, for example, draw a drug from a container and/or deliver medical fluid(s) to one or more patients. One example of such a connector is a rubber septum provided on a conventional drug vial and a needle for withdrawing a quantity of the drug from the drug vial. Each time the drug vial is accessed for the purpose of withdrawing a quantity of the drug therefrom, the rubber septum is typically disinfected with a disinfectant, such as alcohol. The user then pierces the rubber septum with a needle to withdraw a quantity of the drug from the drug vial. After withdrawing the needle from the rubber septum, the elastic nature of the septum material re-seals the drug vial thereby maintaining a sealed connection between the interior and exterior of the drug vial. The user may then utilize the needle to deliver the drug to the patient. In this example, the needle may be considered to be a single use connector that is used only once for each patient and then disposed of as medical waste.

Another example of a medical connector is a swabbable valve and a corresponding single use connector. In this example, the user must swab the connection valve with a disinfectant, such as alcohol, to clean the connection surface before mating the connection valve to the single use connector. The single use connector may be a luer fitting. Commonly, swabbable valves must be swabbed for at least 15 seconds with a disinfectant, after which a waiting period of at least 45 seconds is required for the disinfectant to evaporate. In practice, it is often the case that the connection valve is not disinfected for a proper length of time, if at all.

Conventional medical connectors are generally provided in pre-sterilized, sealed packages prior to use. A user, such as a medical practitioner, must remove the medical connector prior to use. While it is possible to maintain sterility in manufacturing and packaging of medical connectors, various sources of contamination may be introduced as soon as the medical connector is removed from the pre-sterilized, sealed package. For example, airborne particles, such as germs in droplets from coughs or sneezes, may accumulate on a fluid connection element of the medical connector, thereby contaminating it. Spores and dust are additional airborne particulates that may contaminate the medical connector. In use, the medical connector may be contaminated by inadvertent contact with a non-sterile material, such as the clothing or body of a medical practitioner or a patient. Sterility may be further compromised in the process of making a connection between a medical connector and a medical container by touching a non-sterile surface.

Even though various medical connectors of myriad designs have been used for many years, they are associated with a number of drawbacks. During use, it is essential that all contact with non-sterile surfaces is avoided and that exposure to airborne contaminants is reduced, minimized, or eliminated. Each time a fluid connection is established between a medical article, such as a syringe, a dosage container, or a pump, and a fluid line connected to a patient, such as connected to a catheter inserted into the patient, a new, sterile medical connector should be used to connect the fluid line between the medical article and the patient. However, sterility of connection between various medical connector components is often compromised once the medical connector is taken from a sterile environment, such as its packaging. Conventional medical connectors are often provided with dust caps to prevent inadvertent contact with non-sterile surfaces or airborne contaminants. For example, U.S. Pat. No. 2,780,243 (Williams et al.) and U.S. Pat. No. 3,987,930 (Fuson) disclose respective embodiments of stackable or nestable dust caps that are suitable for extended storage, and U.S. Pat. No. 4,778,447 (Velde et al.) discloses a medical connector with both male and female protective caps. However, these means of maintaining sterility are not always utilized in practice. Additionally, providing dust caps on each connector component increases the complexity of such articles, making them prohibitively costly in many instances due to their single use nature as well as increasing the amount of waste requiring disposal.

Various two-piece medical connectors are also known in the medical field, such as from U.S. Pat. No. 4,981,469 to Whitehouse et al. and U.S. Pat. No. 7,241,285 to Dikeman Whitehouse et al. is directed to an assembly for connection to a medicant supply tube and includes a septum assembly including a distal end cap, a septum cap, and an external adapter. Dikeman discloses a medical connector for connecting a fluid passage device, such as may be provided by a luer taper, and an injection site having a thin diaphragm. The medical connector includes a reduced diameter cannula for engaging the thin diaphragm sufficiently to open the thin diaphragm to establish an open fluid passage. U.S. Pat. No. 6,911,025 to Miyahara is directed to a dialysis connector in which a patient side connector is enclosed by a long term use protective cap which encloses a sterile inner cap that is replaced at the conclusion of each dialysis procedure.

Each of the foregoing designs is based on single use connector that the user must replace before making a new fluid connection between a medical article and a patient. Because of their single use design, conventional medical connectors require the user to ensure that proper sterilization precautions are taken each time a new connection is required. Additionally, there exists a significant risk of contamination due to human error in placing and removing dust caps from single use connectors. Furthermore, because no parts of conventional medical connector designs are reusable, large stockpiles of medical connectors must be kept on premises, which increase storage costs and per procedure costs.

The discussion has centered upon the fluid supply side of the fluid delivery system. There are similar or even greater issues, needs, and problems on the patient receiving side where because of the physical pain or discomfort to the patient and the healthcare worker's difficulty of getting vascular access to the patient, there is often the need for sequential delivery or withdrawal of fluids from a single patient vascular access device over the time of their treatment. This is currently solved by using swabbable valves mentioned above or needleless septa. Both of these have significant problems as described above. In addition, it is desirable to have features that reduce the opportunity for blood from a patient to get into the environment.

SUMMARY OF THE INVENTION

In view of the foregoing, a need exists for a medical connector assembly for retaining sterility of a reusable or multi-use connector or element. For example, the medical connector assembly may be used to establish a fluid connection between a first medical device and a second medical device. In one embodiment, the medical connector assembly comprises a multi-use connector and a plurality of single-use connectors connected in series. The multi-use connector has a proximal end opposite a distal end along a longitudinal length thereof. The plurality of single-use connectors each has a proximal end opposite a distal end along a longitudinal length thereof. The distal end of the multi-use connector is releasably connected to the proximal end of a first of the serially-connected single-use connectors. When a second of the serially-connected single-use connectors is disconnected from the first single-use connector, the first single-use connector remains connected to the multi-use medical connector as a sterile cover. Removable caps may be provided to cover the distal end of the multi-use connector and the proximal end of the first single-use connector for sterility, such as prior to use.

A sheath may be disposed about the medical connector assembly and may comprise a first sheath element having a frangible connection to a second sheath element. The sheath may extend over the exterior of the medical connector assembly to extend from the multi-use connector and continue along the serially-connected single use connectors. When the second of the serially-connected single-use connectors is disconnected from the first single-use connector, the sheath is disrupted such that the second single-use connector cannot be easily reattached, or is entirely prevented from being reattached, to the first single-use connector. After the disruption, the first sheath element may remain disposed about the first single-use connector and a portion of the multi-use medical connector and the second sheath element may remain disposed about the disconnected second single-use connector such that the second single-use connector cannot be easily reattached, or is entirely prevented from being reattached, to the first single-use connector.

A fluid path element may be connected to the distal end of the second single-use connector. The fluid path element may comprise a low pressure connector tube adapted for connection to a catheter. The multi-use connector may be provided on a syringe neck connection of a syringe.

Another embodiment described in detail herein is directed to a method of establishing and retaining a sterile fluid connection in a medical connector assembly. The method may comprise providing a multi-use connector comprising a proximal end opposite a distal end along a longitudinal length thereof, and providing a plurality of single-use connectors connected in series and each comprising a proximal end opposite a distal end along a longitudinal length thereof. The method may further comprise connecting the distal end of the multi-use connector to the proximal end of a first of the serially-connected single-use connectors. Further, the method may further comprise disconnecting a second of the serially-connected single-use connectors from the first single-use connector, such that the first single-use connector remains connected to the multi-use medical connector as a sterile cover.

A removable cap may be provided on the distal end of the multi-use connector for sterility, and the method may further comprise removing the cap prior to the step of connecting the distal end of the multi-use connector to the proximal end of the first single-use connector. Additionally, a removable cap may be provided on the proximal end of the first single-use connector for sterility, and the method may further comprise removing the cap prior to the step of connecting the distal end of the multi-use connector to the proximal end of the first single-use connector.

A sheath may be disposed about the medical connector assembly and comprise a first sheath element having a frangible connection to a second sheath element. When the second single-use connector is disconnected from the first single-use connector, the frangible connection is broken. The sheath may extend over the exterior of the medical connector assembly to extend from the multi-use connector and continue along the serially-connected single-use connectors. Further, when the second of the serially-connected single-use connectors is disconnected from the first single-use connector, the sheath is disrupted such that the second single-use connector cannot be easily reattached, or is entirely prevented from being reattached, to the first single-use connector. After the disruption, the first sheath element may remain disposed about the first single-use connector and a portion of the multi-use medical connector and the second sheath element may remain disposed about the disconnected second single-use connector to be disposed of with the second-single use connector.

The method may include providing a fluid path element connected to the distal end of the second single-use connector. The fluid path element may comprise a low pressure connector tube adapted for connection to a catheter. The multi-use connector may be provided on a syringe neck of a syringe. Alternatively, the multi-use connector may be on any type of fluid path element, such as a container, a tube from a supply of medical fluid and the opposing single-use connector may be on the neck of a syringe.

The step of disconnecting the second single-use connector from the first single-use connector may comprise twisting the second single-use connector relative to the first single-use connector and axially detaching the second single-use connector from the first single-use connector.

The multi-use connector and each one of the plurality of serially-connected single-use connectors may comprise an internal flow control element.

The step of connecting the distal end of the multi-use connector to the proximal end of the first of the serially-connected single-use connectors may be accomplished in a sterile airflow. The sterile airflow may be generally parallel or generally perpendicular to an intended fluid flow direction through the medical connector assembly. For example, the sterile airflow may be generally parallel or generally perpendicular to a direction of approach between the multi-use connector and the opposing single-use connector.

In another embodiment, a medical connector assembly is provided comprising a multi-use connector and a plurality of single-use connectors connected in series. The multi-use connector is releasably connected to a first of the serially-connected single-use connectors and when a second of the serially-connected single-use connectors is disconnected from the first single-use connector, the first single-use connector remains connected to the multi-use medical connector as a sterility retaining cover.

The multi-use connector may be provided on a discharge neck of a syringe.

The first single-use connector may be in threaded engagement with the multi-use connector.

The first single-use connector may be comprised of two connector elements fitted together in interfering engagement.

A frangible sheath may be disposed about the medical connector assembly and comprise a first sheath element having a frangible connection along a circumferential notch to a second sheath element.

The second single-use connector may be adapted to break apart along a circumferential notch such that, upon breaking, a portion of the second single-use connector is retained with the opposing first single-use connector.

The second single-use connector may be comprised of a first connector element and a second connector element, with the first connector element defining a head portion comprising a depending portion adapted for sliding engagement into a mating receptacle defined in the second connector element. A frangible sheath may secure the first connector element in engagement with the second connector element.

The second single-use connector may be comprised of a first connector element and a second connector element, with the first connector element defining a head portion and the second connector element comprising opposed folding elements that fold over the head portion. A frangible sheath may secure the first connector element in engagement with the second connector element.

The second single-use connector may be comprised of a first connector element and a second connector element in abutting engagement held together by a frangible shrink wrap sheath, such as shrink wrap, an over-molded clamp, a clamp with a living hinge and catch, a spring clip, or another similar element, apparatus, or methodology in which intentional exertion force is used to overcome a retention force.

The first single-use connector may be in threaded engagement with the multi-use connector, and a threaded sheath may be in threaded engagement with the first single-use connector. The threaded engagement between the sheath and the first single-use connector may be oppositely operated from the threaded engagement between the first single-use connector and the multi-use connector. The second single-use connector may be in threaded engagement with the sheath to secure the second single-use connector in series with the first single-use connector.

The single-use connectors may be integrally formed and adapted to break into at least two elements along a circumferential notch.

A sheath may be disposed about the medical connector assembly and comprise a first sheath element having a frangible connection to a second sheath element. The sheath may extend over the exterior of the medical connector assembly to extend from the multi-use connector and continue along the serially-connected single use connectors. Further, when the second single-use connector is disconnected from the first single-use connector, the first sheath element may remain disposed about the first single-use connector and a portion of the multi-use medical connector, and the second sheath element remains disposed about the disconnected second single-use connector.

Further details and advantages will be understood from the following detailed description read in conjunction with the accompanying drawings figures.

BRIEF DESCRIPTION OF THE DRAWINGS

FIG. 5 is a block diagram view of the medical connector assembly of FIG. 3 shown in conjunction with a stream of sterile air that flows generally parallel to the direction of fluid flow through the medical connector assembly.

FIG. 6 is a block diagram view of the medical connector assembly of FIG. 3 shown in conjunction with a stream of sterile air that flows generally perpendicular to the direction of fluid flow through the medical connector assembly.

FIG. 38 is an exploded perspective view of another embodiment of the medical connector assembly associated with an angiographic syringe.

DETAILED DESCRIPTION OF THE INVENTION

Figure 1:
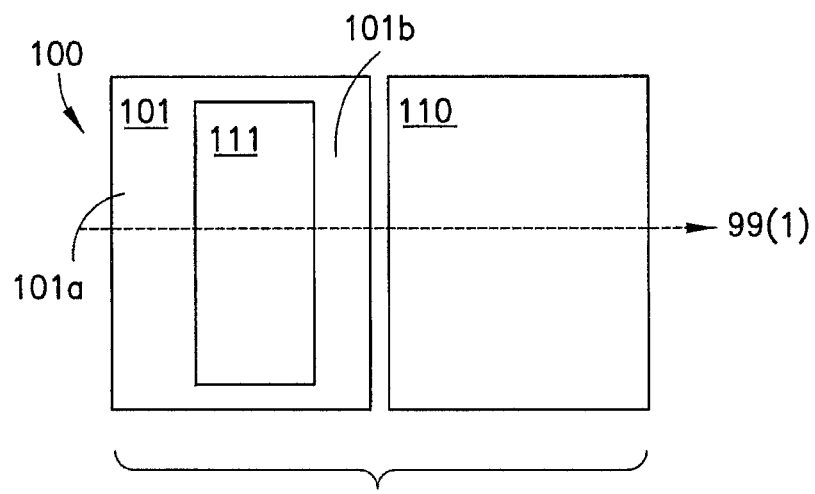
FIG. 1 is a block diagram view of an embodiment of a multi-use connector assembly.

For purposes of the description hereinafter, spatial orientation terms, if used, shall relate to the referenced embodiment as it is oriented in the accompanying drawing figures, or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting. The terms "longitudinal" and "serial" as used in connection with relationship of parts, features, or elements in this disclosure, while generally illustrated as straight lines in the figures, are not intended to be exclusively limited to linear or straight line relationships.

Referring to the figures in which like reference characters refer to like parts throughout the several views thereof, a medical connector assembly 10 (hereinafter "connector assembly 10") and method for retaining sterility of a reusable portion of the connector assembly 10 will be described herein in detail. With initial reference to FIGS. 1-3, the assembled connector assembly 10, as shown in FIG. 3, generally comprises a multi-use connector assembly 100 removably coupled to a single-use connector assembly 200. As described in detail herein, the single-use connector assembly 200 includes a plurality of single-use connector elements 201, 202, for example sequentially connected together in series to form a chain, a fluid path, or a fluid channel Each single-use connector element 201, 202 (hereinafter "single-use connectors 201, 202") is generally a hollow, tubular structure made from a material suitable for medical applications, such as medical grade plastic. Similarly, the multi-use connector assembly 100 comprises a multi-use connector element 101 (hereinafter "multi-use connector 101") that is generally a hollow, tubular structure made from a material suitable for medical applications, such as medical grade plastic. It may be desirable to construct the multi-use connector 101 and/or the single-use connectors 201, 202 from a clear medical grade plastic in order to facilitate visual verification that a fluid connection has been established between these elements of the connector assembly 10 and visually detect the presence of air in the connector assembly 10. Additionally, one or more fluid path elements 300, such as medical tubing 302 in an exemplary embodiment, may be provided with (e.g., part of) or be connected to the single-use connector assembly 200 to enable fluid communication between the multi-use connector 101 and the downstream fluid path element 300 via the single-use connector assembly 200. The fluid path element 300 may alternatively be a catheter or other similar fluid path element.

With specific reference to FIG. 1, the multi-use connector assembly 100 is shown in a state after removal from its packaging (not shown). The multi-use connector assembly 100 is desirably packaged in a pre-sterilized, sealed package that protects the multi-use connector assembly 100 from contamination with air or surface-borne contaminants. The multi-use connector assembly 100 generally comprises a multi-use connector 101 and a removable dust cap 110 which protects the multi-use connector assembly 100 from inadvertent contamination as it is removed from the packaging and before it is connected to the single-use connector assembly 200, as described herein. The cap 110 may be air-tight or vented. Additionally, the cap 110 may have a plurality of longitudinal ribs (not shown) on the external sidewall thereof to provide a convenient gripping surface for the user to remove the cap 110 from the multi-use connector 101.

The multi-use connector assembly 100 may be, for example, removably attached to or, alternatively, part of a syringe, fluid pump device, and like fluid delivery devices which are used to deliver fluid under pressure to the downstream fluid path element 300 via the single-use connector assembly 200. Additionally, the multi-use connector assembly 100 may be, for example, removably attached to or, alternatively, part of a medical tubing set, a catheter, or other fluid path or conducting element, which is used to receive multiple sequential doses of fluid including, for example, a catheter or port in a patient. The multi-use connector 101 has a proximal side or end 101a opposite a distal side or end 101b along the longitudinal length of the multi-use connector 101. The proximal side 101a of the multi-use connector 101 is often connected to a fluid source (not shown in FIG. 1), such as a contrast solution container or a drug container or, as indicated in the foregoing, may be removably connected to or be part of a fluid delivery device such as a syringe or fluid pump device that is used to deliver fluid under pressure. The distal end 101b of the multi-use connector 101 is enclosed by the removable cap 110 which protects the distal end 101b of the multi-use connector 101 from inadvertent contamination after it is removed from the packaging. The distal end 101b of the multi-use connector 101 is generally adapted for fixed and fluid-tight connection with one of the single-use connectors 201, 202, namely the proximal-most or upstream single-use connector 201 in the chain of connectors 201, 202 in the single-use connector assembly 200. A dotted arrow 99(1) in FIG. 1 shows the direction of fluid flow through the multi-use connector 101 during use in a fluid delivery procedure. The multi-use connector 101 may optionally include an internal flow control element 111, such as a slit diaphragm or a one-way or two-way check valve, which prevents fluid flow until a sufficient pressure difference across the internal flow control element 111 is reached. In this manner, the flow control element 111 prevents fluid from an associated fluid source container, fluid delivery device (e.g., pump or syringe), or fluid path set, from dripping from the multi-use connector 101.

Alternatively, if flow under low pressure conditions, such as gravity driven flow, is desired, as well as resistance to flow when disconnected, the internal flow control element 111 may be a reflux valve that functions similar to those used in needleless connectors, such that the insertion of the single-use connector assembly 200 opens the internal flow control element 111 so that fluid can flow with minimal pressure differential. Common methods to accomplish this result are shown in Needleless Connectors: A Primer on Terminology, by Lynn Hadaway, MEd, RNC, CRNI® and Deb Richardson, MS, RN, CNS, Journal of Infusion Nursing; VOL 33|NUM 1|January/February 2010 which is incorporated herein by reference.

Figure 2:
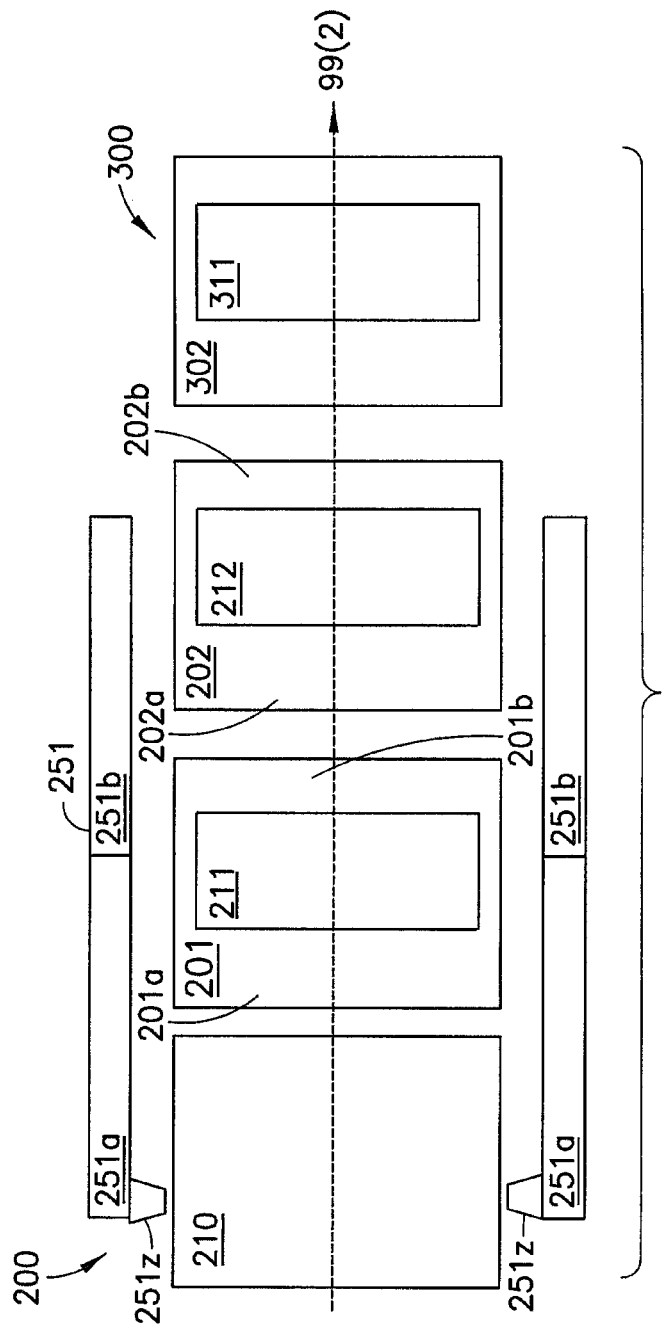
FIG. 2 is a block diagram view of an embodiment of a single-use connector assembly.
Figure 3:
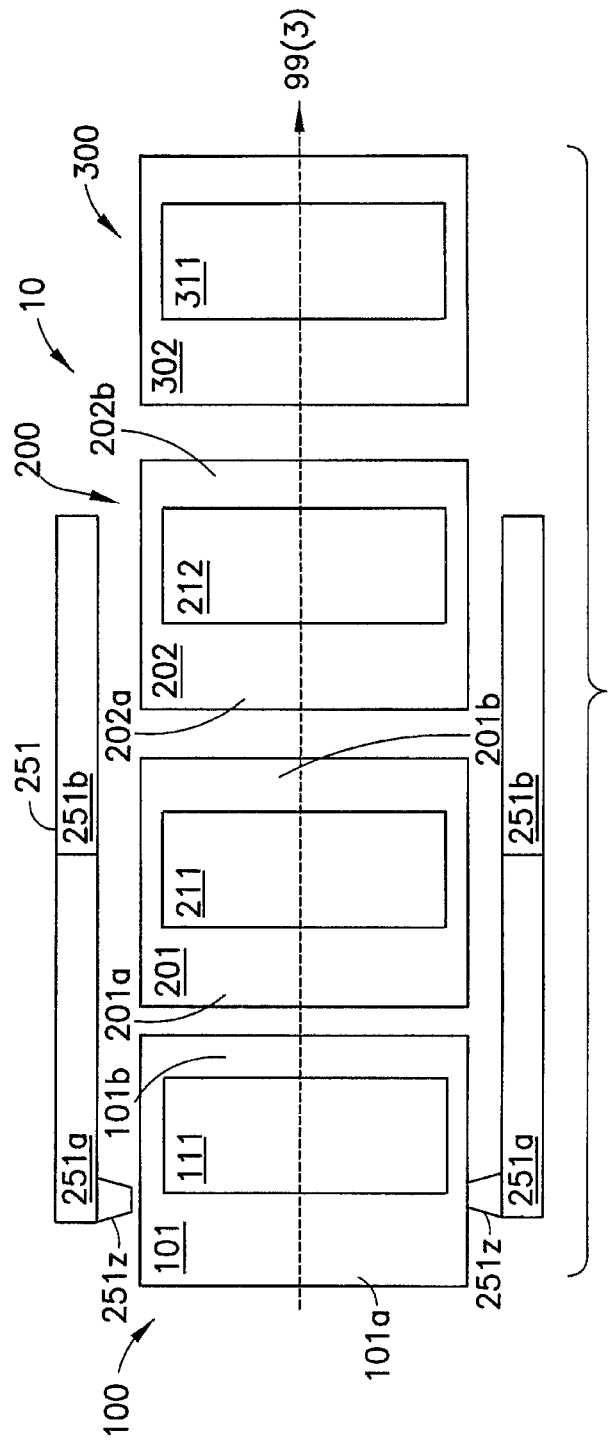
FIG. 3 is a block diagram view of the single-use connector assembly of FIG. 2 shown connected with the multi-use connector assembly of FIG. 1 to form a medical connector assembly.

With reference to FIG. 2, the single-use connector assembly 200 is shown in an initial state after removal from its packaging (not shown). As with the multi-use connector assembly 100 shown in FIG. 1, the single-use connector assembly 200 is desirably packaged in a pre-sterilized, sealed package that protects the single-use connector assembly 200 from contamination with air or surface-borne contaminants. A removable dust cap 210, similar to the cap 110, protects the single-use connector assembly 200 from contamination after it is removed from the packaging and before it is connected to the multi-use connector assembly 100. The cap 210 may be air tight or vented and may include similar gripping features to the cap 110 discussed previously. The caps 110, 210 are desirably provided as sterility retaining caps or covers, but may be any device or feature that helps preserve sterility by reducing the likelihood or preventing accidental contact with surfaces and/or contact by airborne contaminants; suitable embodiments include a dust cap, lid, cover, seal, membrane, sterility retaining cover, or sterility maintaining cover.

The single-use connector assembly 200 generally includes a plurality of single-use connectors 201, 202 sequentially connected together in series to form a chain, a fluid path, or a fluid channel, as mentioned previously. Each single-use connector 201, 202 is generally a hollow, tubular structure made from a material suitable for medical applications, such as medical grade plastic, as noted previously. A dotted arrow 99(2) in FIG. 2 shows the direction of fluid flow through the single-use connector assembly 200 during use in a fluid delivery procedure.

The first or proximal single-use connector 201 has a proximal side or end 201a and a distal side or end 201b. Similarly, the second or distal single-use connector 202 has a proximal side or end 202a and a distal side or end 202b. The proximal end 201a of the first single-use connector 201 in the chain of single-use connectors 201, 202 is protected by the removable cap 210 prior to connection with the multi-use connector 101. The distal end 201b of the first single-use connector 201 is connected to the proximal end 202a of the successive single-use connector 202. In turn, the distal end 202b of the successive single-use connector 202 may be connected to a fluid path element 300 which may be, for example, medical tubing 302, or optionally a catheter fluid path set or other fluid conducting element, a syringe, a fluid pump device, a fluid container, etc. Each single-use connector 201, 202 desirably includes an internal flow control element 211, 212, such as a flexible or resilient slit diaphragm, one-way check valve, reflex valve or other equivalent structure, which prevents fluid flow under low pressures in either direction when the distal end 201b of the first single-use connector 201 is separated from the proximal end 202a of the successive single-use connector 202. The downstream fluid path element 300 may also include a similar flow control element 311 having similar or identical structure and function to the flow control elements 211, 212 in each of the single-use connectors 201, 202. The flow control element 311 of the fluid path element 300 prevents fluid movement under gravity or low-pressure conditions so that when the second single-use connector 202 is ultimately disconnected from the multi-use connector 101, as described herein, minimal or no fluid drips from the fluid path element 300.

Alternatively, if flow under low pressure conditions, such as gravity driven flow, is desired, as well as resistance to flow when disconnected, the internal flow control elements 211, 212, and/or 311 may be reflux valves that function similar to those used in needleless connectors, such that the insertion of the upstream or downstream element(s) opens the internal flow control element(s) so that fluid can flow with minimal pressure differential. The internal flow control element(s) can be designed and come assembled such that they are held in the open position by an upstream or downstream fluid path element and move to the closed position upon separation of that restraining fluid path element.

The fluid path element 300 may be replaced by a suitable removable cap similar to the removable cap 210 connected to the distal end 202b of the second single-use connector 202 if so desired, for example to enable alternative or non-preassembled fluid path elements to be utilized. FIG. 2 further illustrates a sheath 251 comprising a first or proximal sheath element 251a and a second or distal sheath element 251b as an optional element of the single-use connector assembly 200. The sheath 251 is typically frangible and extends over the exterior of the connector assembly 10, preferably extending from the multi-use connector 101 and continuing along the single-use connector assembly 200. The sheath 251 helps prevent accidental or intentional misuse as will be explained hereinafter. The connection of the multi-use connector assembly 100 with the single-use connector assembly 200 optionally having a connected fluid path element 300 forms the overall connector assembly or arrangement 10.

Specific mechanical details of the connection between the multi-use connector 101 and the first single-use connector 201 are not specifically illustrated in FIGS. 1-6 because the connection may be established in a number of ways. For example, the multi-use connector 101 may have a threaded male luer connection and the first single-use connector 201 may have a mating threaded female luer connection, or vice versa. The male or female luer connections may be provided at either the distal or proximal ends of the multi-use connector 101 and within the single-use connectors 201, 202. This specific and non-limiting mating luer connection arrangement is shown in FIGS. 7-12, which will be discussed in greater detail hereinafter.

Another alternative for making a fluid-tight connection between the multi-use connector 101 and the first single-use connector 201, as well as within the connections between the single-use connectors 201, 202, is a bayonet connection where a male end on one of the multi-use connector 101 and the first single-use connector 201 has one or more pins which engage a matching slot provided on the female end of the other of the multi-use connector 101 or the first single-use connector 201. A similar connecting arrangement may be provided between the first and second single-use connectors 201, 202. Alternatively, the connector assembly 10 may include an axial "push and catch" type of connection where the male end on one of the multi-use connector 101 and the first single-use connector 201 is inserted into the female end of the other of the multi-use connector 101 and the first single-use connector 201. Again, a similar connecting arrangement may be provided between the first and second single-use connectors 201, 202. Other possible embodiments of mechanical connection between the various connecting components of the connector assembly 10 include face-sliding attachment, barbed fittings, collet fittings, compression fittings, clamp fittings, and bonding or breakable attachments. One of ordinary skill in the art will recognize that this listing of connection alternatives for making fluid-tight connections between the mating components of the connector assembly 10 is not exhaustive and other equivalent mechanical connecting arrangements may be provided. Additionally, various combinations and permutations of the foregoing-described mechanical connecting arrangements may be employed in accordance with this disclosure. Accordingly, in the depicted embodiment in the accompanying figures, the first single-use connector 201 in the single-use connector assembly 200 is inserted into/onto the multi-use connector 101 of the multi-use connector assembly 100 until a fluid tight connection is established. Next, the fluid path element 300 may be connected to the distal end 202b of the second single-use connector 202, or the fluid path element 300 may be provided as part of, such as integral with, the second single-use connector 202.

The connection between the mating elements of the connector assembly 10 may also include a seal (not shown) at the interface between the mating elements. For example, a seal may be provided at the proximal end, the distal end, or both on the multi-use connector 101 and/or the single-use connectors 201, 202. The seal forms a fluid-tight connection between the mating elements and prevents fluid from a fluid source container, a fluid delivery device, medical tubing, etc., from dripping through the interface between the mating elements of the connector assembly 10. In one exemplary embodiment, the seal may be a taper seal which is formed between a tapering surface on a first mating element and a tapering surface on the opposing second mating element of the connector assembly 10 as is done with a conventional luer connector. Alternately, the seal may be in the form of a face seal or an O-ring provided on the mating surface of a mating element. Further, the seal may be formed by heating the mating elements or otherwise bonding them to create a fluid-tight connection. Further, the seal may be accomplished by multi-shot molding, over molding, or by incorporating the function of the two connectors into one physical piece which "breaks" upon separation.

In the single-use connector assembly 200, the sheath 251 is generally provided to increase the reliability and/or improve human factor reliability of the attachment and detachment process between the multi-use connector 101 and the single-use connectors 201, 202. In one embodiment, as shown in FIGS. 1-3, the sheath 251 is separated into a first sheath element 251a and a second sheath element 251b by serrations for frangibility, as mentioned previously. The sheath 251 may also contain gripping members 251z on the proximal end of the first sheath element 251a that are adapted to grip the exterior of the multi-use connector 101. As noted previously, the multi-use connector 101 may be a fluid delivery device such as a syringe or a fluid pump device, or could also be another fluid conducting component such as a valve port on a stopcock valve, etc. In use, as the first single-use connector 201 is attached to the multi-use connector 101, the gripping members 251z on the first sheath element 251a are attached to the multi-use connector 101 in a non-rotationally removable manner. As an example, the gripping members 251z could be ratchets or ramped elements that slide over oppositely faced ramps on the exterior surface of the multi-use connector 101 to allow the single-use connectors 201, 202 to be rotated for attachment, but do not allow rotation for the detachment of the first single-use connector 201 from the multi-use connector 101. Alternatively, the gripping members 251z can be metal teeth or barbs which are slanted such that they rotate freely in one direction and dig into the wall of the multi-use connector 101 and prevent rotation in the other direction, or which are positioned and angled to allow motion proximally onto the multi-use connector 101 but prevent motion in the distal direction. In this manner, when it is desired to remove the second single-use connector 202 from connection with the first single-use connector 201, the user grips the second sheath element 251b and twists. This twisting motion tears serrations or a thinned element or section (not shown) thereby separating the second sheath element 251b from the first sheath element 251a and, further, separates the first single-use connector 201 from the adjoining single-use connector 202, with the first single-use connector 201 remaining in fluid connection with the multi-use connector 101. The single-use connector 201 that remains connected to multi-use connector 101 now serves the function of a removable "cap" for the multi-use connector 101. The removed single-use connector 202 and any connected fluid path element 300 may be safely disposed of as medical waste. When it is desired to connect a "new" single-use connector assembly 200 to the multi-use connector 101, it is only necessary to remove the remaining single-use connector 201 from the multi-use connector 101. In this example, the first sheath element 251a may be short enough so that the operator can grip just the remaining single-use connector 201 and twist to disconnect it from the multi-use connector 101. The first sheath element 251a can then be pulled off axially from the multi-use connector 101 as the retained "cap" single-use connector 201 is removed. Optionally, the sheath 251 generally, or the sheath element 251b in particular, may be configured to cooperate with structures on the multi-use connector 101 or the single-use connectors 201, 202 so that it is difficult or impossible to simply and reliably reconnect the second single-use connector 202 to the first single-use connector 201 for use with subsequent patients.

Alternatively, rather than having the sheath 251 separate into two parts during the removal of the single-use connector 202, the sheath 251 may split, stretch, or otherwise act so that the single-use connector 202 can be removed. Such action by the sheath 251 helps ensure that the single-use connector 202 is preferentially removed from the single-use connector 201 rather than the single-use connector 201 being removed from the multi-use connector 101. The action of the sheath 251 also helps reduce the likelihood that a connector of some type may be reattached to the distal end 201b of the single-use connector 201 either accidentally or intentionally. The goals of reducing the likelihood that the single-use connector 201 is removed before the single-use connector 202 and helping to prevent the reattachment of a connector onto the distal end 201b of the single-use connector 201 can also be accomplished by design features external to the overall connector assembly or arrangement 10. For example, once the single-use connector 200 is attached to the multi-use connector 101, a feature on a fluid injector or its housing could grasp the single-use connector 201 so that it cannot be removed until the user takes some action, optionally removing the single-use connector 202. Additional mechanical or electromechanical strategies known to those skilled in the medical arts may be used to accomplish this interlocking or mistake-reducing function.

Figure 4:
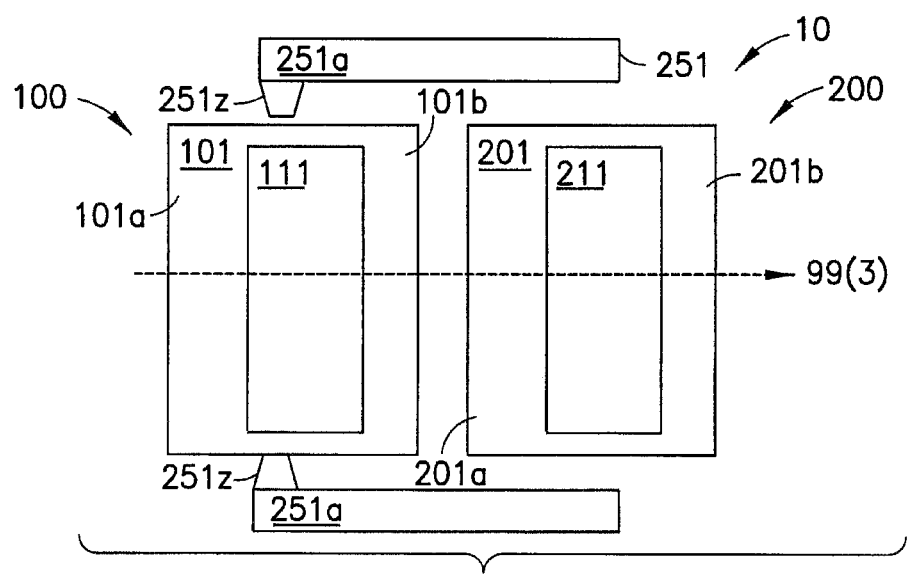
FIG. 4 is a block diagram view of a portion of the medical connector assembly shown in FIG. 3.

In summary, referring specifically to FIG. 3, the overall connector assembly or arrangement 10 is shown. In exemplary use of the connector assembly 10, the single-use connector assembly 200 is connected to the multi-use connector assembly 10. Such a connection is established by removing the cap 110 from the multi-use connector 101, for example in a flow of sterile air as described herein, removing the cap 210 from the first single-use connector 201, and then mating the multi-use connector 101 to the first single-use connector 201. Once a secure fluid tight connection between the foregoing connector elements is made, fluid from a fluid source or a fluid delivery device may be delivered to the fluid path element 301 via the single-use connector assembly 200, and either immediately or ultimately to a patient as desired. In one particular application, a programmable power fluid injector or an infusion pump may be used to deliver a predetermined amount of fluid from an associated fluid delivery device (e.g., a syringe or a pump cassette). Such a fluid delivery apparatus is capable of developing sufficient pressure to drive fluid through the low-pressure restrictions of the plurality of flow control elements 111, 211, 212, and/or 311 if they are provided in the flow path of the fluid. Alternatively, some or all of the flow control elements 111, 211, 212, and/or 311 may be absent or may be biased open when the respective connector elements are connected to allow flow at very low pressures or to allow the measurement of downstream pressures, for example blood pressure in the patients. After completion of a fluid delivery procedure and/or when it is desired to remove the second single-use connector 202 from connection with the first single-use connector 201, the user grips second sheath element 251b and twists. This twisting motion tears serrations (not shown) separating the second sheath element 251b from the first sheath element 251a and, further, separates the first single-use connector 201 from the adjoining single-use connector 202, with the first single-use connector 201 remaining in fluid connection with the multi-use connector 101, as shown in FIG. 4. The single-use connector 201 that remains connected to the multi-use connector 101 now serves the function of a removable sterile "cap" for the multi-use connector 101.

A further technique for preserving the sterility of the multi-use connector 101 during attachment therewith of the single-use connector assembly 200 having two (2) or more single-use connectors 201, 202 will now be described with additional reference to FIGS. 5-6. As described previously, each assembled connector assembly 10 includes a multi-use connector 101 and a plurality of single-use connectors 201, 202 in secure fluid connection with each other. The first single-use connector 201 is coupled to the multi-use connector 101, while the second single-use connector 202 is coupled to the preceding single-use connector 201, as described previously. The initial connection between the first single-use connector 201 and the second single-use connector 202 is desirably established during the manufacture and packaging of the single-use connector assembly 200. As such, it is possible to closely monitor and control the production environment and ensure that a "pre-coupled" sterile connection is present between the first single-use connector 201 and the second single-use connector 202.

Once the multi-use connector assembly 100 and the single-use connector assembly 200 are removed from their packaging, these components are joined together to form the connector assembly 10. During the connection step for connecting the first single-use connector 201 to the multi-use connector 101, it may be desirable to join the multi-use connector 101 to the single-use connector 201 in an enhanced sterile environment. FIG. 5 shows this connecting step between the first single-use connector 201 and the multi-use connector 101 in conjunction with a stream of sterile air 450. The use of sterile air 450 in making the connection between the multi-use connector 101 and the single-use connector 201 provides an additional measure of sterility protection by reducing the likelihood of airborne particulates accumulating on the mating surfaces of the first single-use connector 201 and the multi-use connector 101 between the time the protective caps 110, 210 are removed and the connection between these elements is completed. In FIG. 5, the stream of sterile air 450, which may be created by a fan and a HEPA filter with a preferred filtering capacity, is directed through air plenum 410 to flow over the multi-use connector 101 in a direction that is generally parallel to the fluid flow axis 99(3) along the longitudinal length of the connector assembly 10. In this manner, the multi-use connector 101 is disposed in a stream of sterile air even when the caps 110, 210 are removed in the process of making a connection with the first single-use connector 201. The stream of sterile air 450 may be operating continuously or may be selectively turned on during the connection process and then selectively turned off to conserve energy and filter life once the connection is made. The air plenum 410 may be part of a housing of a power fluid injector (not shown) that accepts a syringe to which, for example, the multi-use connector 101 is attached. A controller associated with the power fluid injector may operate the air plenum 410 in the manner described in the foregoing.

With reference to FIG. 6, an alternative embodiment is shown in which the stream of sterile air 450 is generally perpendicular to the general fluid flow direction along the fluid flow axis 99(3) and to the common connection direction. This alternative embodiment has a benefit in that it may be easier for the user to ensure the sterility of the connection by removing the cap 210 from the first single-use connector 201 in sterile air, dispose of the cap 210, and then make a connection to the multi-use connector 101 in a downward stream of air. The stream of sterile air 450 may also use part of the housing of a power fluid injector (not shown) as part of air plenum 410 or be incorporated as a separate hood or air plenum structure.

Figure 7:
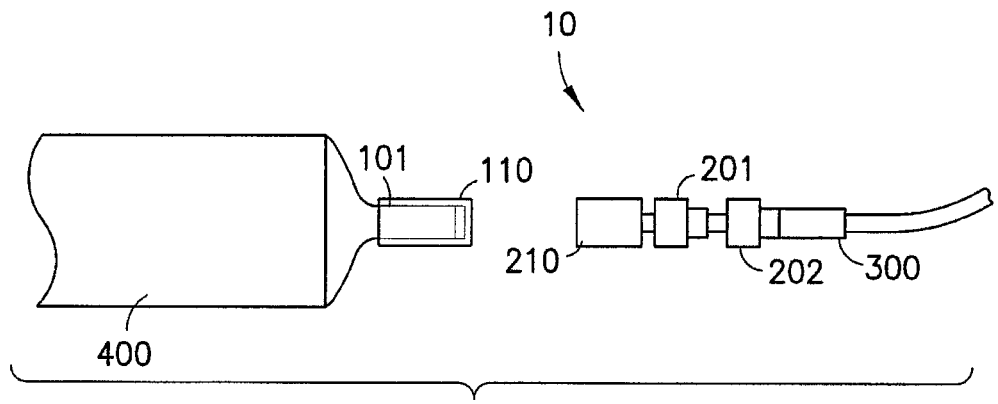
FIG. 7 is a schematic view of the medical connector assembly prior to connection of the single-use connector assembly of FIG. 2 with the multi-use connector assembly of FIG. 1.
Figure 8:
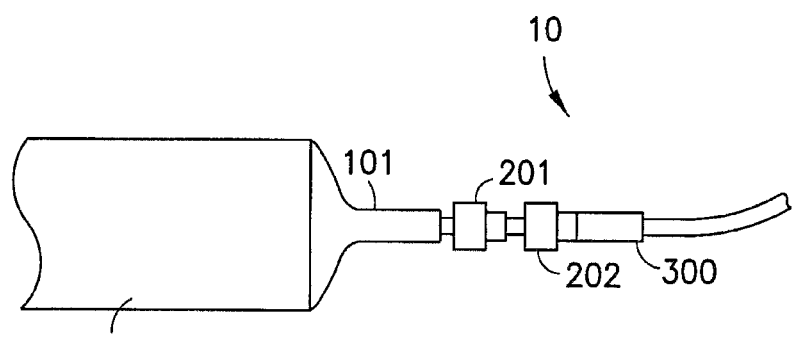
FIG. 8 is a schematic view of the medical connector assembly of FIG. 7 after connection of the single-use connector assembly of FIG. 2 with the multi-use connector assembly of FIG. 1.
Figure 9:
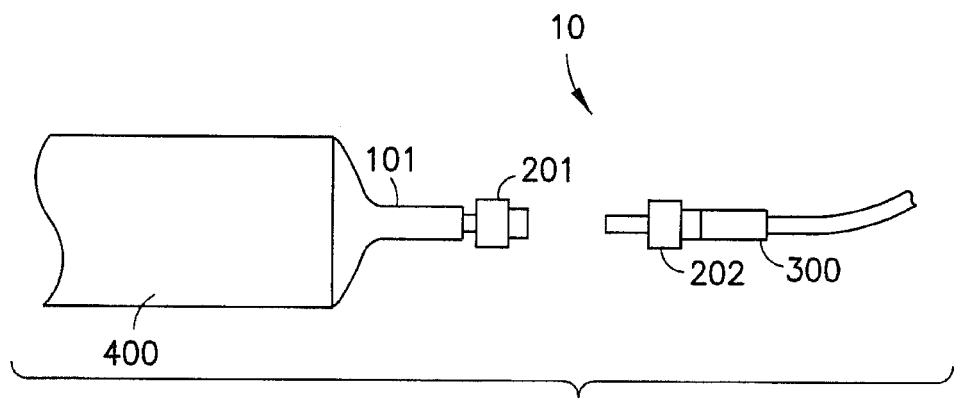
FIG. 9 is a schematic view of the medical connector assembly of FIG. 7 after the single-use connector assembly has been partially disassembled so that a portion of the single-use connector assembly and the multi-use connector assembly may be discarded.

With reference to FIGS. 7-9, a general operational sequence for assembling and disassembling the connector assembly 10 is shown. In FIGS. 7-9, the multi-use connector 101 with attached removable cap 110 is shown connected with a fluid delivery device such as a syringe 400 for a power fluid injector (not shown). The single-use connector assembly 200, as described previously, includes a first single-use connector 201 covered by a cap 210, a connected second single-use connector 202, and, further, a fluid path element 300 connected to the second single-use connector 202. As an example, the fluid path element 300 may be low pressure connector tubing 302 adapted for connection to a catheter. FIG. 8 shows that the removable cap 110 has been removed from the multi-use connector 101, the removable cap 210 has been removed from first single-use connector 201, and the first single-use connector 201 is connected to the multi-use connector 101, which permits fluid communication between the syringe 400 and the fluid path element 300. Referring next to FIG. 9, the second single-use connector 202 is shown disconnected from the first single-use connector 201, leaving the first single-use connector 201 in place connected to the multi-use connector 101 for sterility purposes. The second single-use connector 202 and attached fluid path element 301 may be discarded as medical waste.

Figure 10:
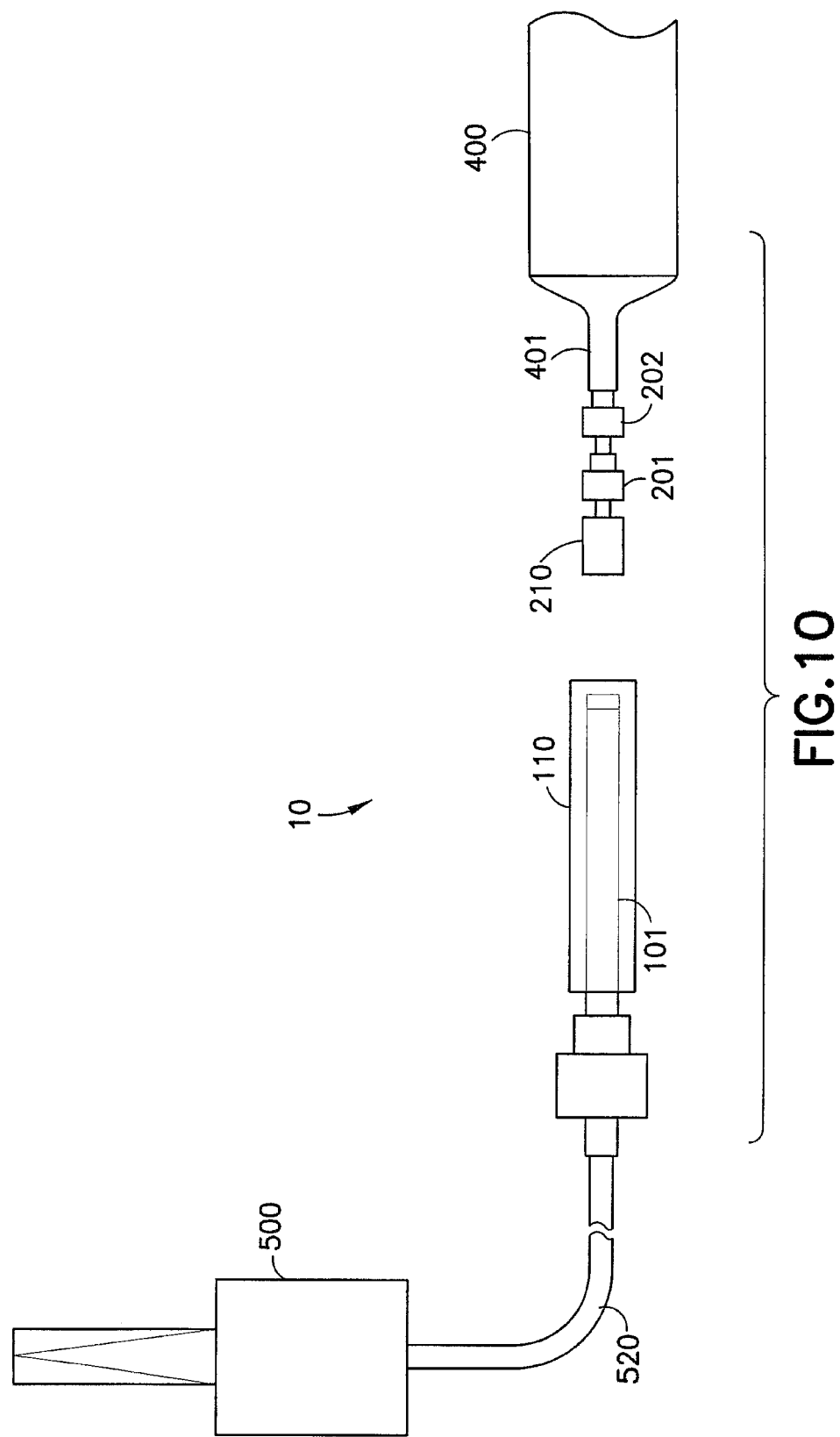
FIG. 10 is a schematic view of the medical connector assembly prior to connection of the single-use connector assembly of FIG. 2 with the multi-use connector assembly of FIG. 1, and further shown in an environment for filling a syringe with fluid.
Figure 11:
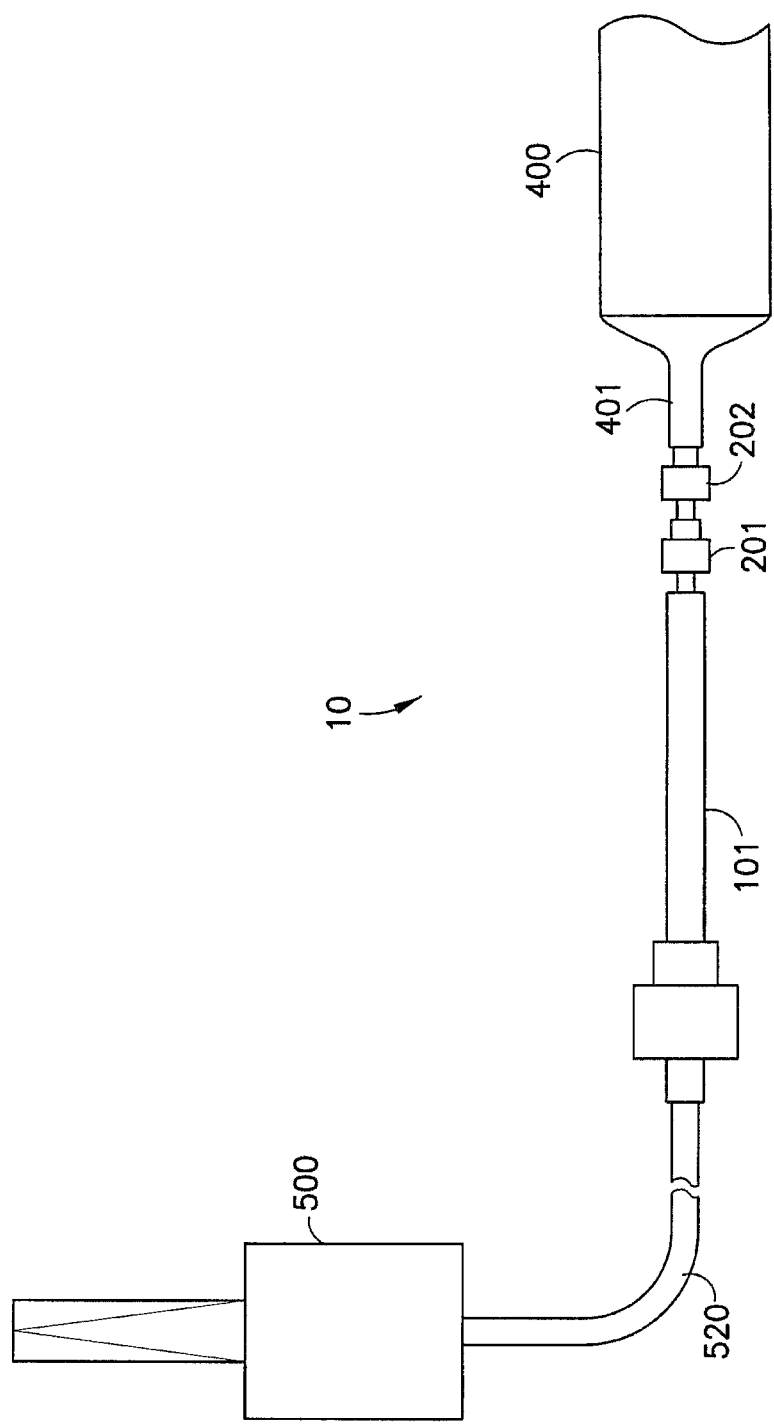
FIG. 11 is a schematic view of the medical connector assembly of FIG. 10 after connection of the single-use connector assembly of FIG. 2 with the multi-use connector assembly of FIG. 10.
Figure 12:
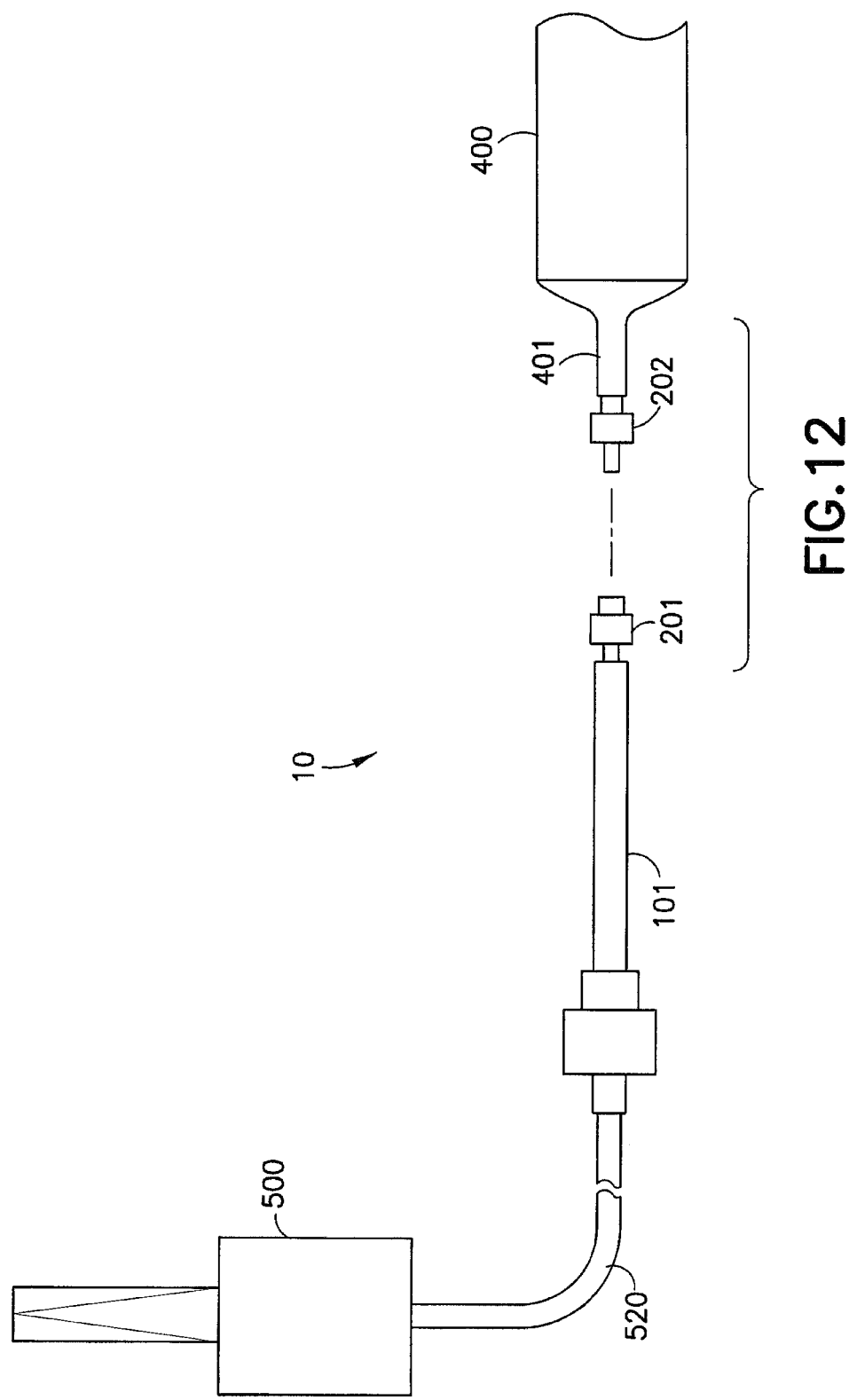
FIG. 12 is a schematic view of the medical connector assembly of FIG. 10 after the single-use connector assembly has been partially disassembled so that a portion of the single-use connector assembly and the multi-use connector assembly may be discarded.

Referring next to FIGS. 10-12, an embodiment is shown that is specifically adapted for the filling syringes. In FIGS. 10-12, a spike 500 is connected by medical tubing 520 to the multi-use connector 101. The spike 500 is used for connection to a pharmacy bulk pack (not shown) and like containers from which contrast or other drugs may be drawn to fill multiple syringes for multiple patients. The single-use connector assembly 200 comprising single-use connectors 201, 202 may be used to establish fluid communication between the multi-use connector 101 and fluid path element 301, in this case the syringe neck connection 301 of a syringe 400. The connection operation in the present embodiment is exactly the same as described previously, wherein the first single-use connector 201 remains behind to protect the sterility of the multi-use connector element 101. When the second single-use connector 202 is separated from the first single-use connector 201, the second single-use connector 202 and the syringe 400 remain connected, thus preserving the sterility of the syringe neck connection 401 of the syringe 400, which may subsequently be placed in a fluid injector. Once the syringe 400 is loaded in a fluid injector, the single-use connector 202, which is serving as a cap on the syringe neck 401, is removed and the syringe neck 401 can be directly connected to tubing (not shown) to carry the fluid in the syringe 400 to a single patient, or the syringe neck connection 401 may be considered to "become" the multi-use connector 101 of FIGS. 1 and 3 and be used with methods and devices of this disclosure to deliver fluid to a plurality of patients. The use of sterile airflow in the manner described previously, may be used in the present syringe-filling illustration to further enhance sterility when making the above-described connections.

In a typical application of the connector assembly 10 in a fluid delivery procedure, once the fluid delivery procedure is completed using the multi-use connector 101, single-use connector assembly 200, and fluid path element 300, the proximal end 202a of the "downstream" single-use connector 202, which is furthest away from the multi-use connector 101, is removed from the distal end 201b of the first single-use connector 201. This removal also removes the "used" fluid path element 300 along with the "downstream" single-use connector 202. Once the "used" distal-most single-use connector 202 and fluid path element 300 are removed from the adjoining or upstream single-use connector 201, the connection assembly 10 is ready for subsequent reuse, if so desired. The first single-use connector 201 remains attached to the multi-use connector 101 as shown in FIG. 4. This remaining single-use connector 201 now performs a similar function to the dust cap 110, described previously, which is to retain sterility of the multi-use connector 101. Next, in order to make a second connection to the multi-use connector 101, a "new" single-use connector assembly 200, such as that shown in FIG. 2, is removed from its packaging. The cap 210 is removed from the "new" single-use connector 201, and the "used" single-use connector 201 is removed from the multi-use connector 101. The multi-use connector 101 and the "new" single-use connector 201 may be mated as before to form a new connection for delivery of fluid involving the same or a new patient. This procedure may be repeated until the fluid supply runs out or the fluid path upstream of the multi-use connector 101 needs to be changed for any reason, such as reaching a preset permitted number of uses, procedures, time, or patients.

Figure 13:
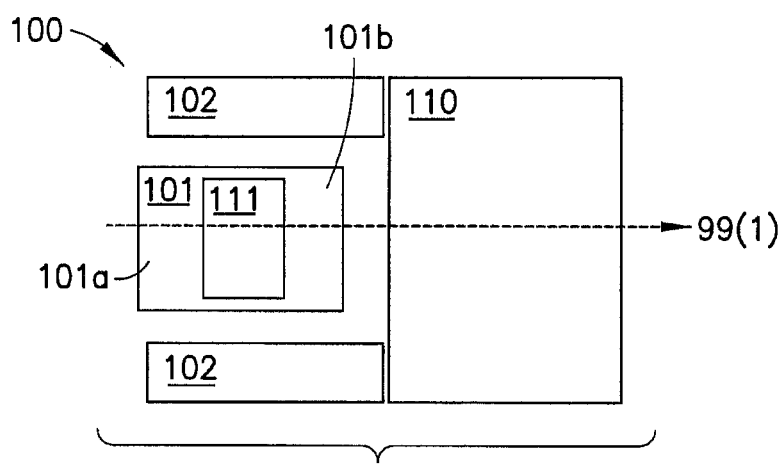
FIG. 13 is a block diagram view of another embodiment of the multi-use connector assembly of FIG. 1.
Figure 14:
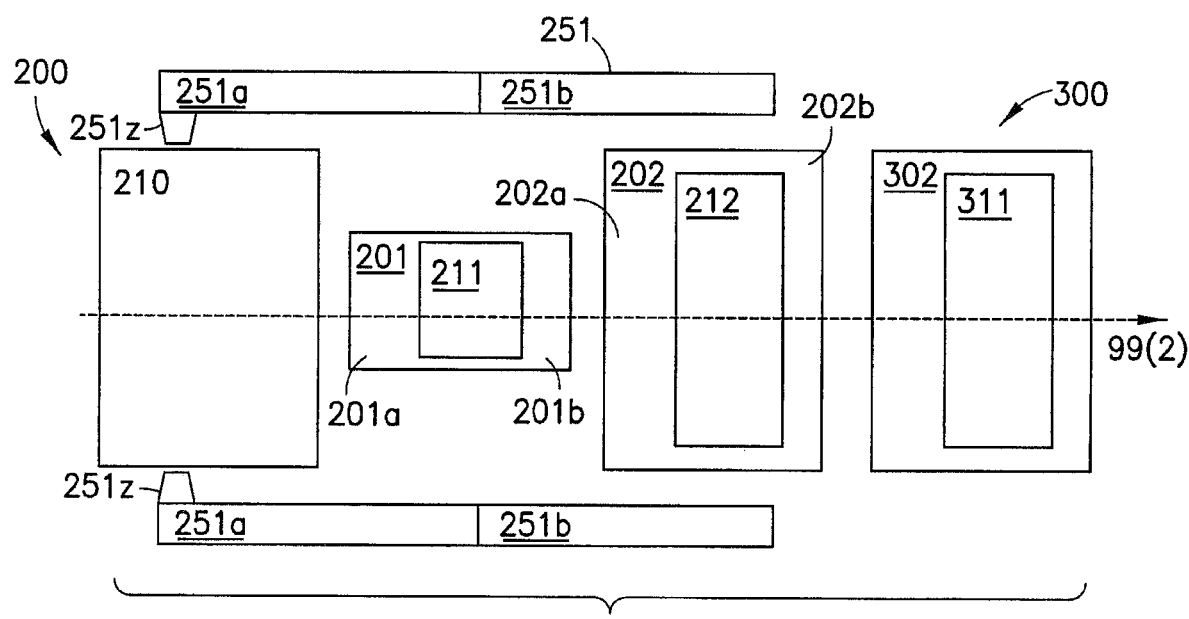
FIG. 14 is a block diagram view of another embodiment of the single-use connector assembly shown in FIG. 2.
Figure 15:
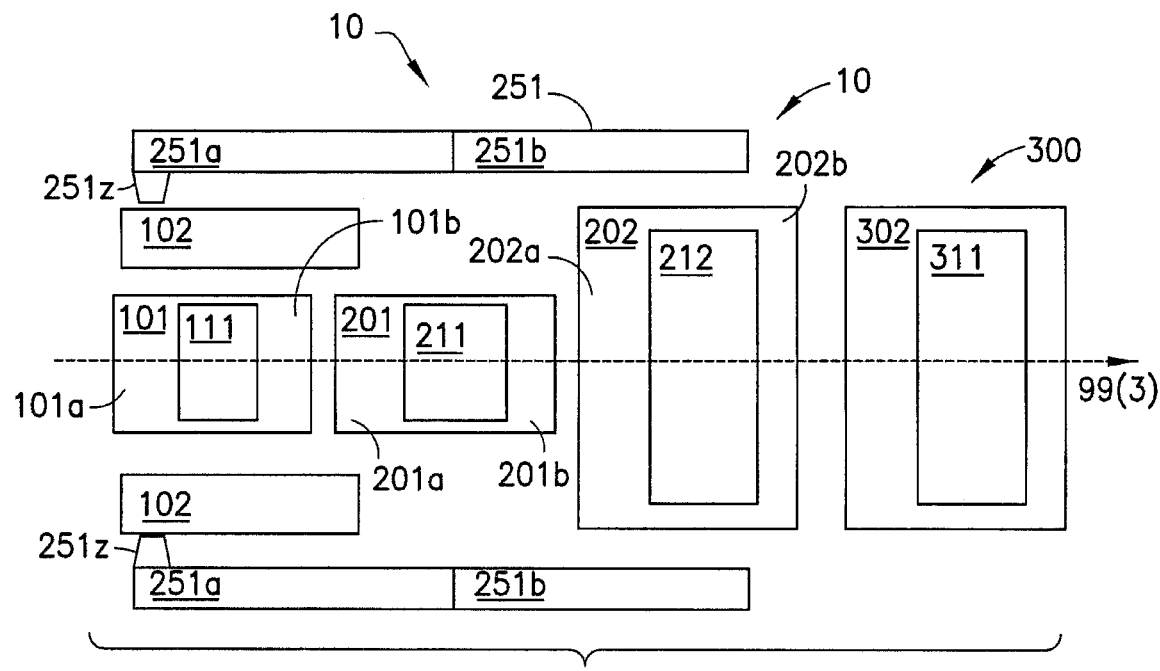
FIG. 15 is a block diagram view of the single-use connector assembly of FIG. 14 shown connected with the multi-use connector assembly of FIG. 13 to form another embodiment of the medical connector assembly.

Referring next to FIGS. 13-15, FIG. 13 shows an embodiment that adds another feature to multi-use connector assembly 100 in the form a preferably cylindrical, coaxial guard 102 which makes it more difficult for there to be inadvertent contact with the sterile multi-use connector 101 by recessing the multi-use connector 101 into the guard 102. FIG. 14 shows a corresponding modification to the single-use connector assembly 200 in which the first single-use connector 201 is sized to fit within the cylindrical, coaxial guard 102 and form a sealed fluid path with the multi-use connector 101. When the dust covers 110 and 210 are removed from their respective connectors, as single-use connector assembly 200 is brought towards multi-use connector assembly 100, the guard 102 prevents the potentially non-sterile aspects of single-use connector assembly 200, for example, sheath 251, from touching the sterile aspects of multi-use connector assembly 100, which is multi-use connector 101. FIG. 15 shows the assembled fluid path, with multi-use connector 101 sealably mated with the first single-use connector 201 and thus able to transmit fluid to the remainder of the fluid path elements. This embodiment and others described hereinafter may optionally have the dust caps 110, 210 provided as simple flat sheets of material that can be adhesively or heat sealed onto the respective connector assemblies 100, 200 and simply peeled-off by the user.

Figure 16:
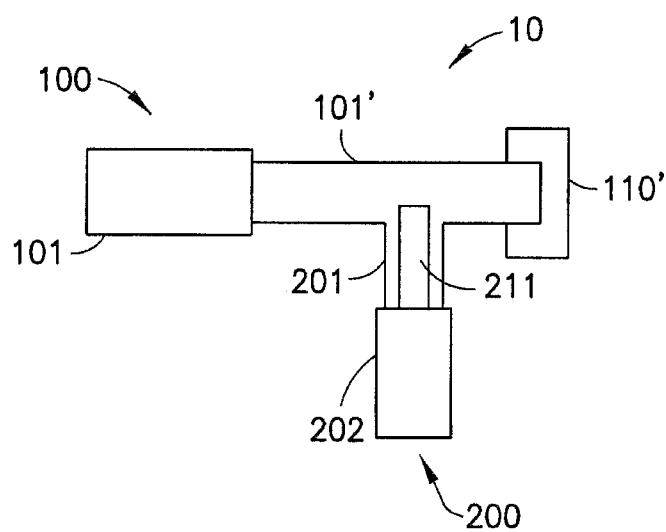
FIG. 16 is a schematic view of another embodiment of the medical connector assembly.
Figure 17:
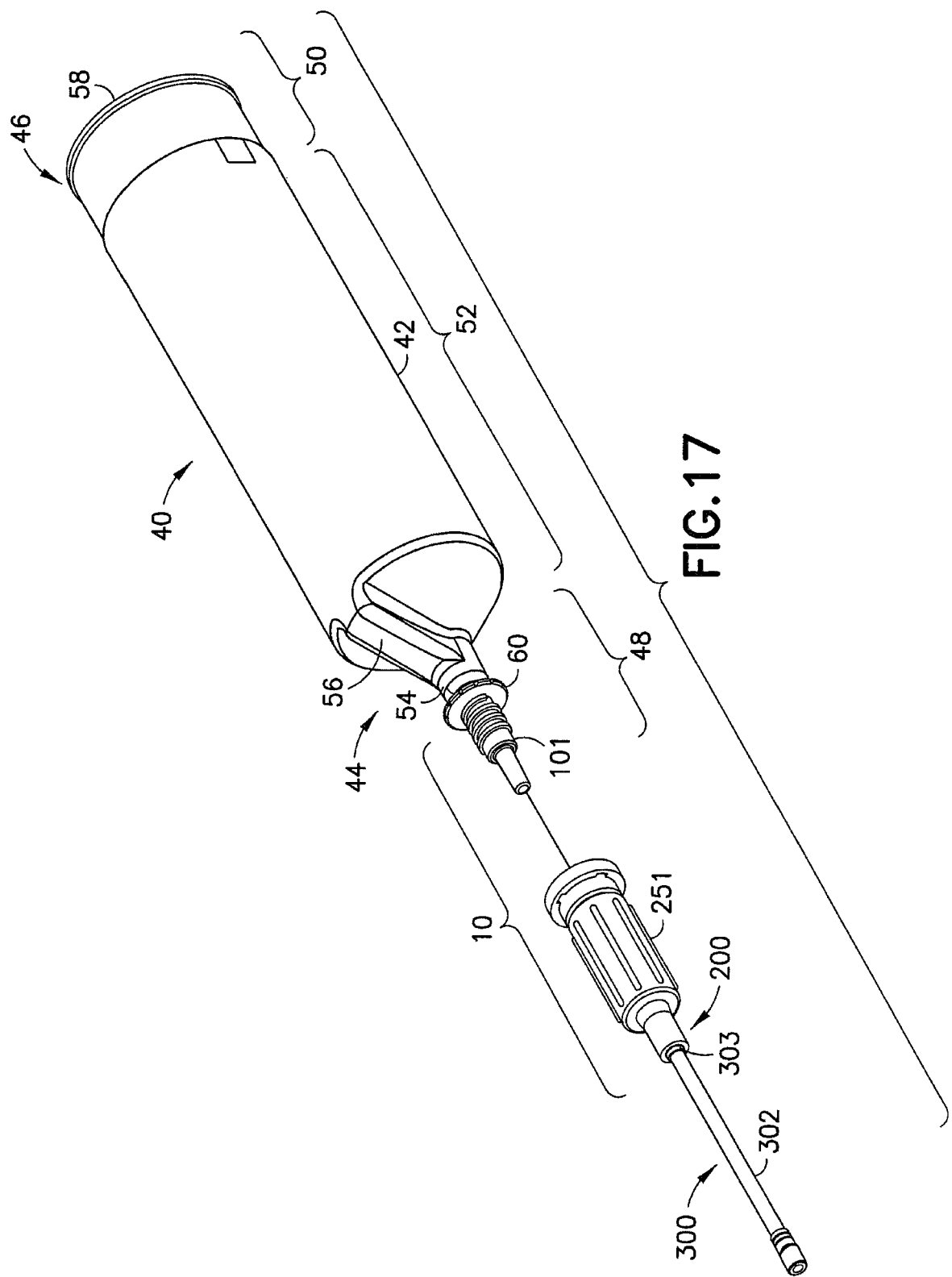
FIG. 17 is an exploded perspective view of another embodiment of the medical connector assembly suited for high pressure applications such as with an angiographic syringe.
Figure 18:
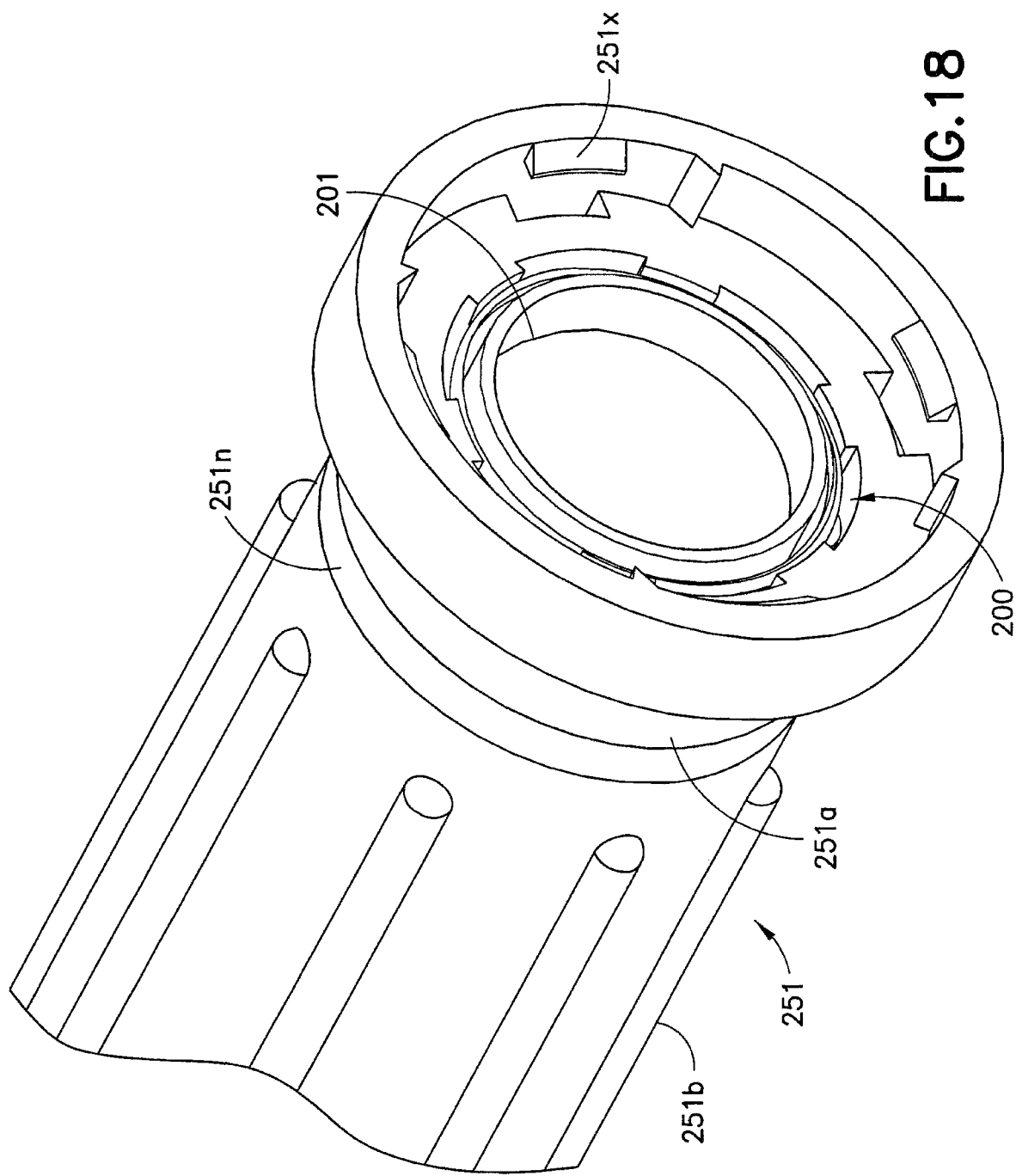
FIG. 18 is a perspective end view of the single-use connector assembly used in the medical connector assembly of FIG. 17.
Figure 19:
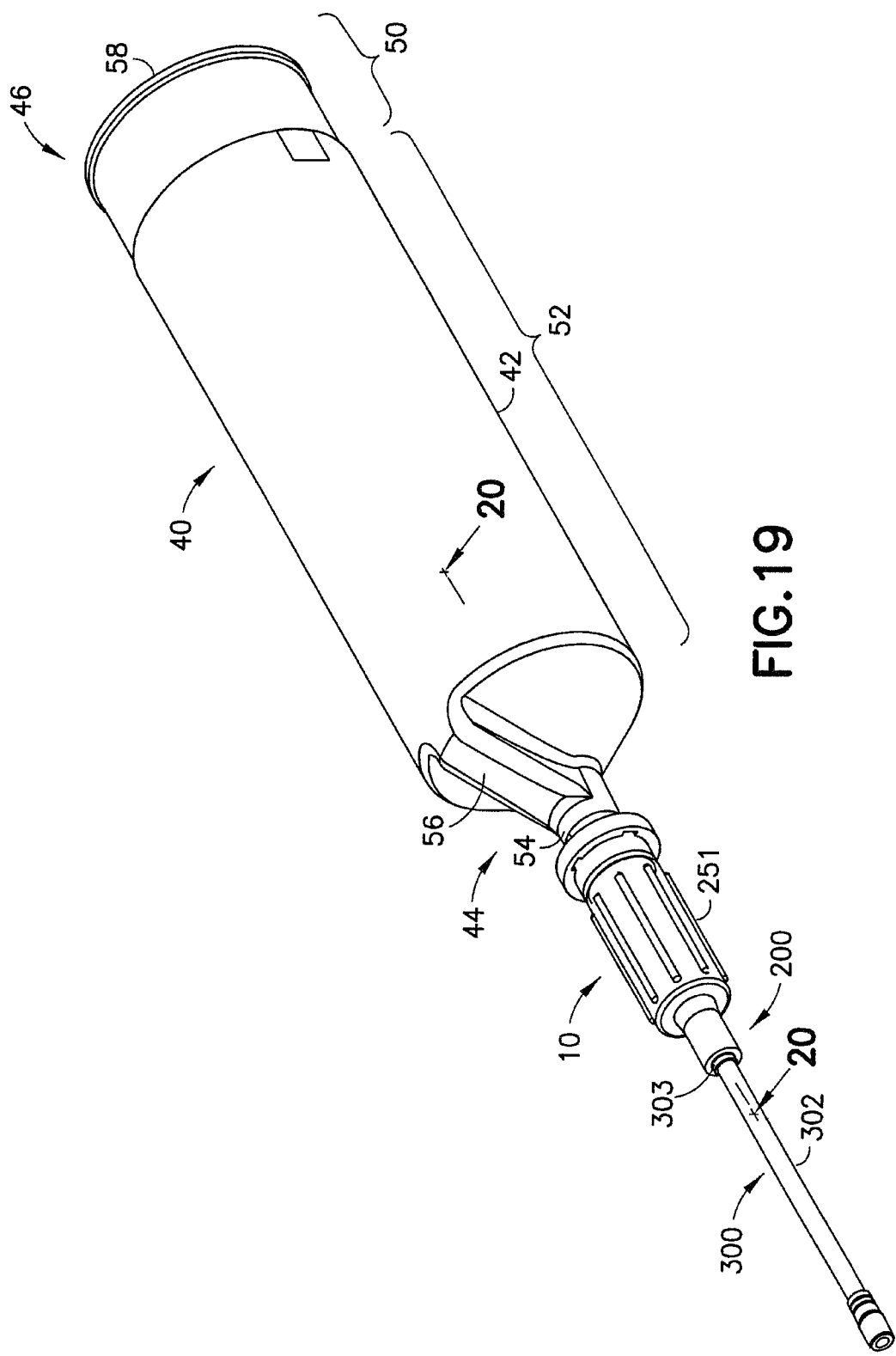
FIG. 19 a perspective view of the medical connector assembly and syringe shown in FIG. 17.
Figure 20:
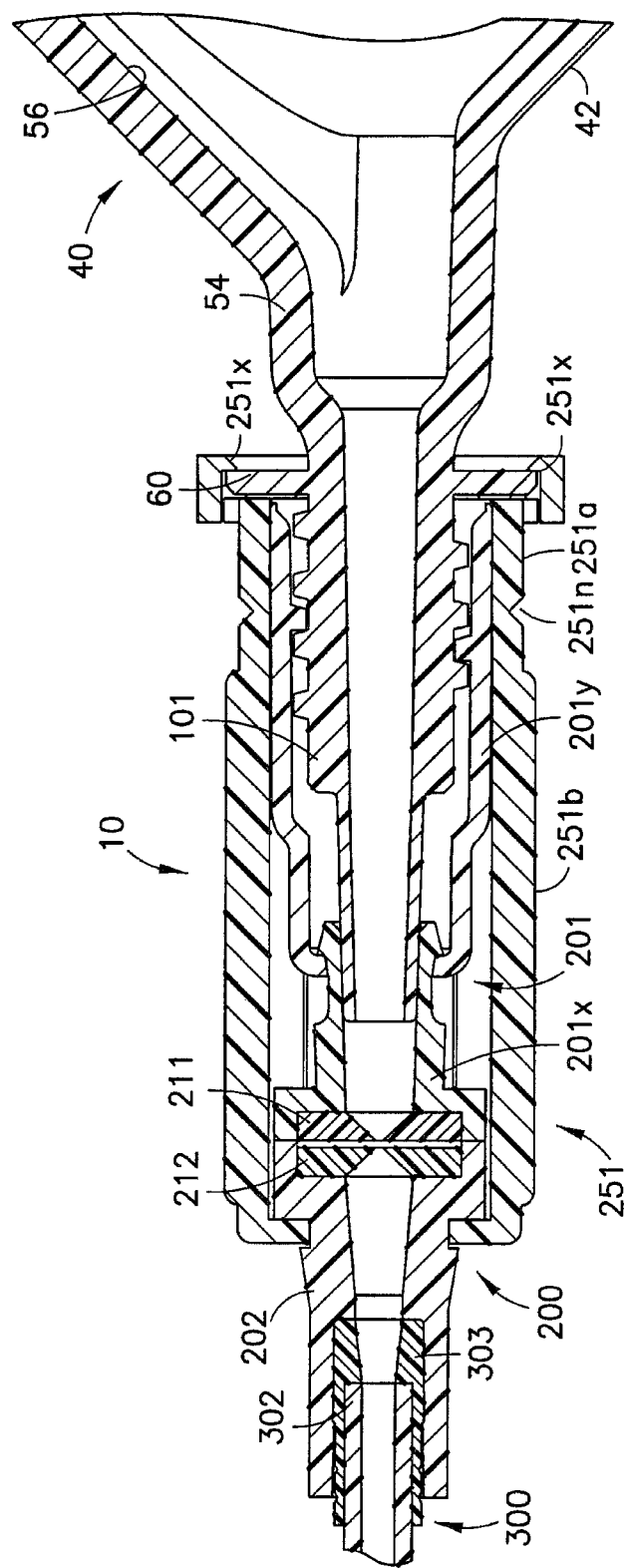
FIG. 20 is a cross-sectional view taken along line 20-20 in FIG. 19.
Figure 21:
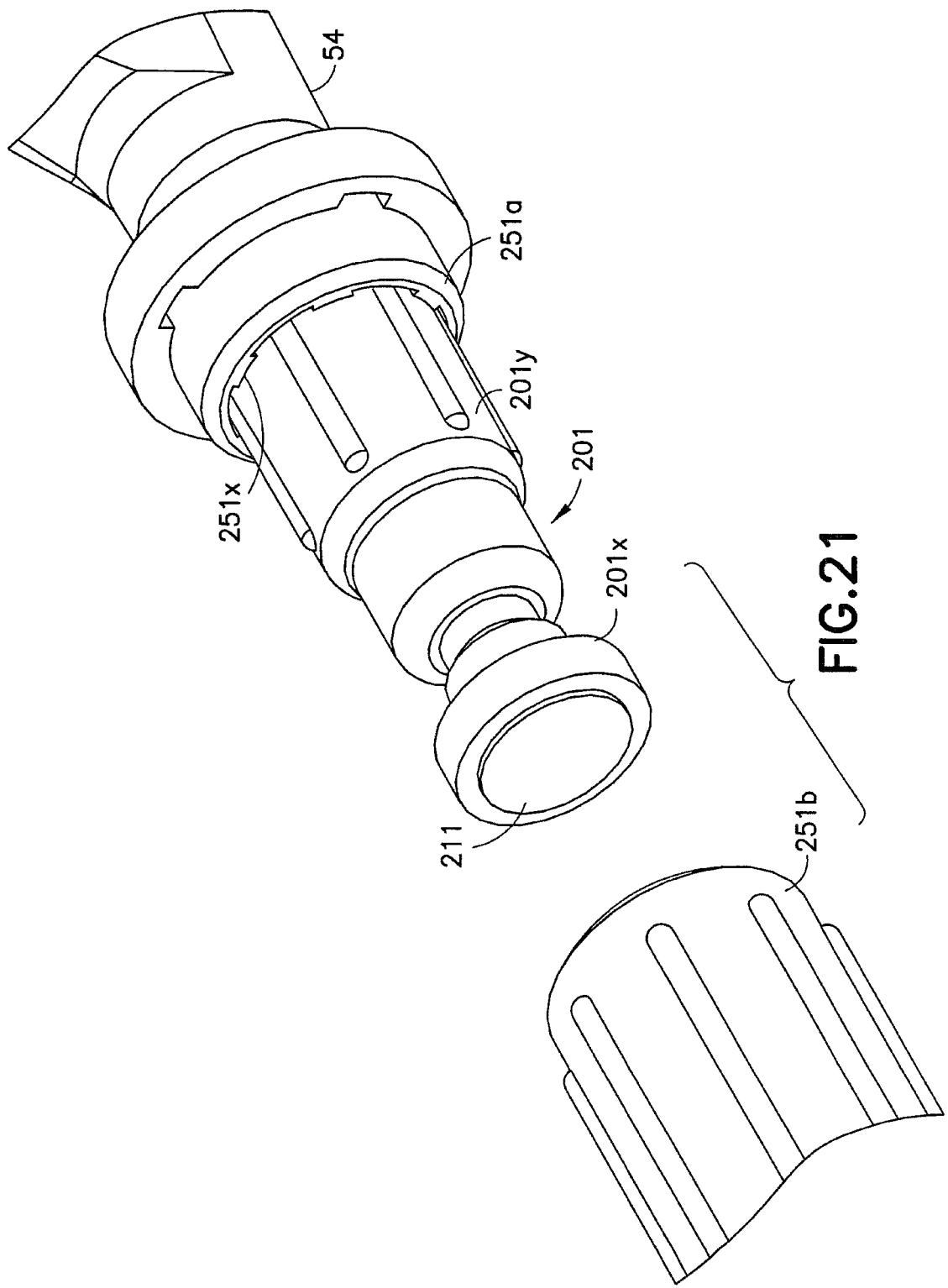
FIG. 21 is an exploded perspective view showing the single-use connector assembly of the medical connector assembly of FIG. 17.
Figure 22:
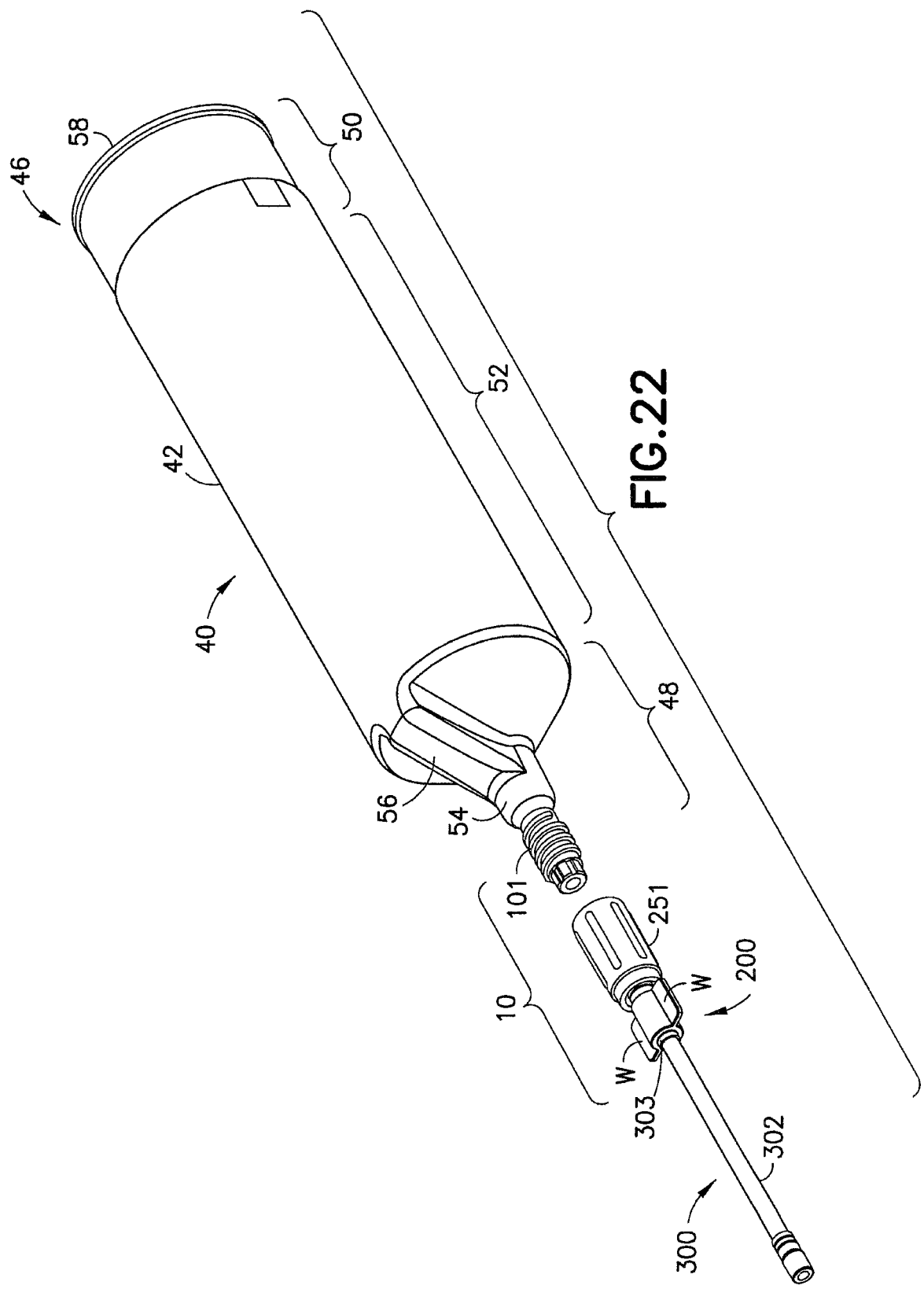
FIG. 22 is an exploded perspective view of another embodiment of the medical connector assembly in which a frangible connection may be provided as part of the single-use connector assembly.
Figure 23:
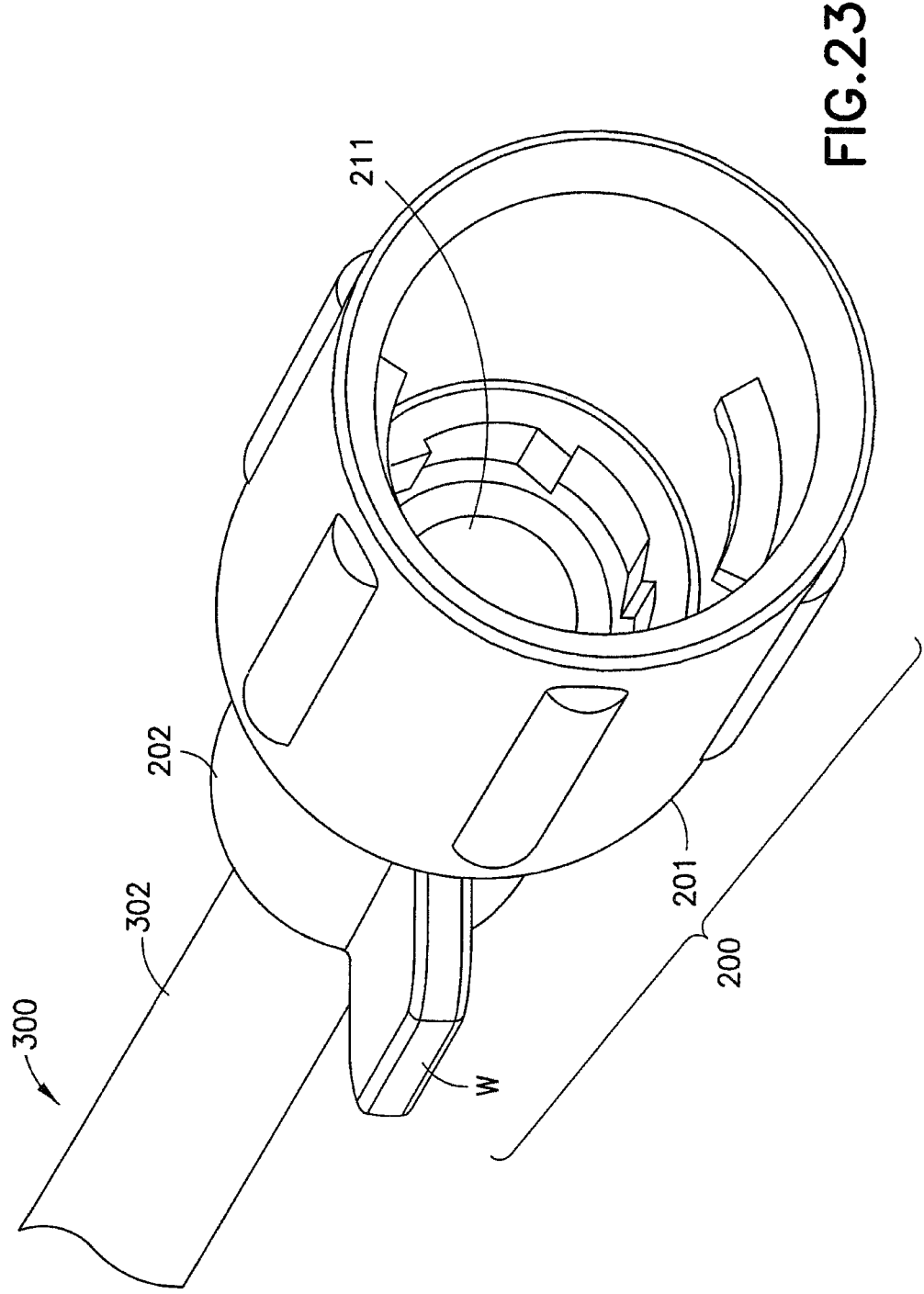
FIG. 23 is a perspective end view of the single-use connector assembly used in the medical connector assembly of FIG. 22.
Figure 24:
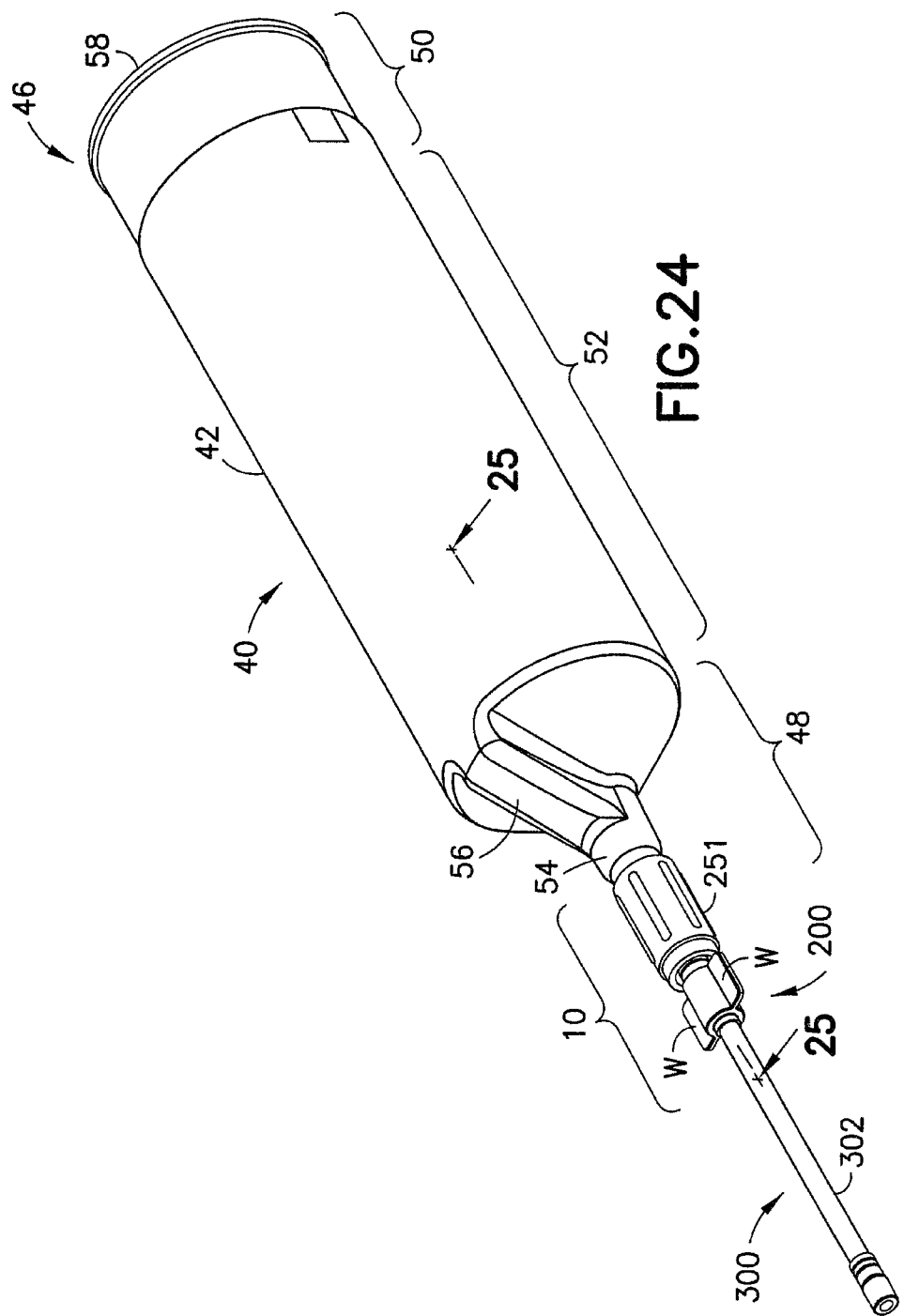
FIG. 24 a perspective view of the medical connector assembly and syringe shown in FIG. 22.
Figure 25:
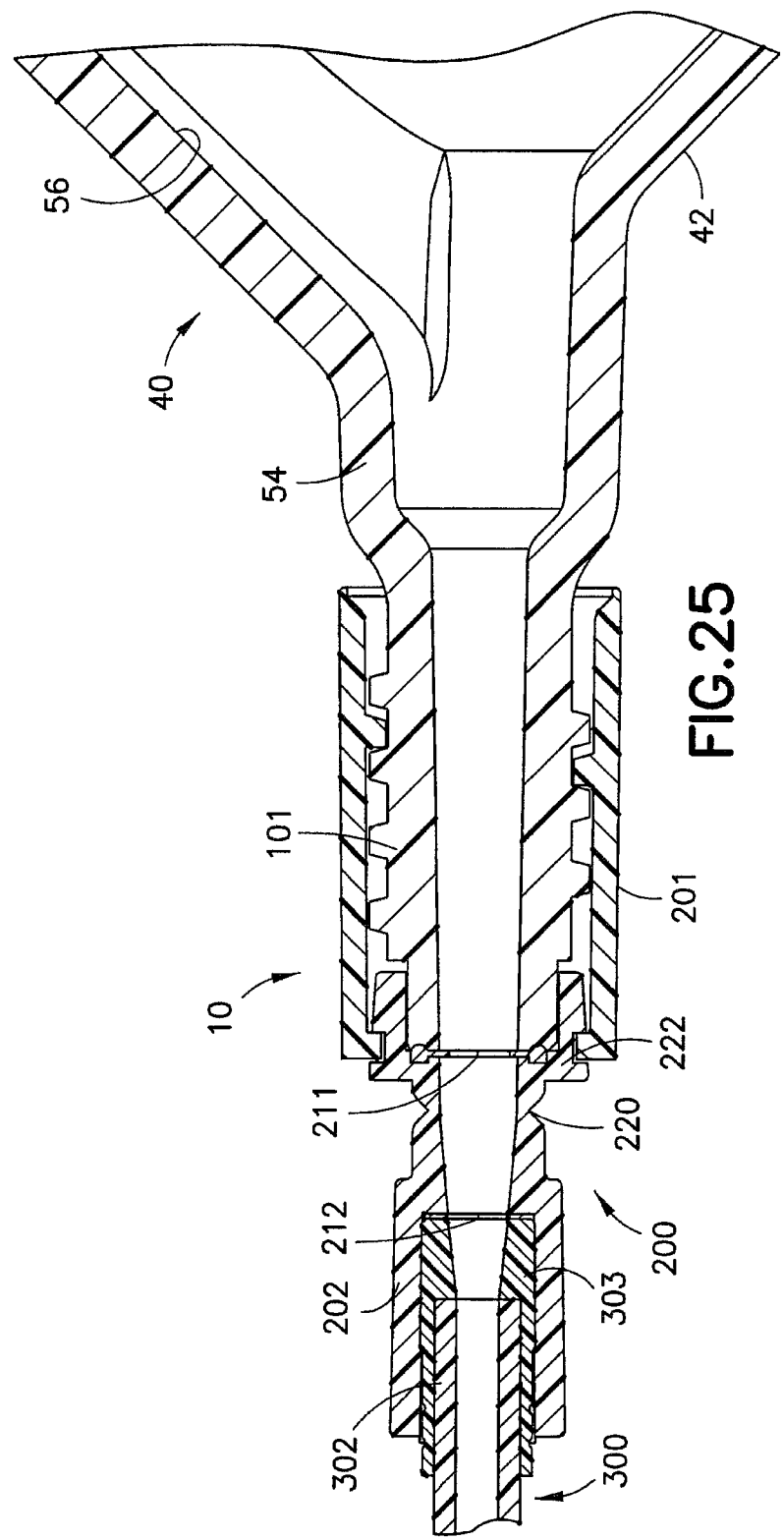
FIG. 25 is a cross-sectional view taken along line 25-25 in FIG. 24.
Figure 26:
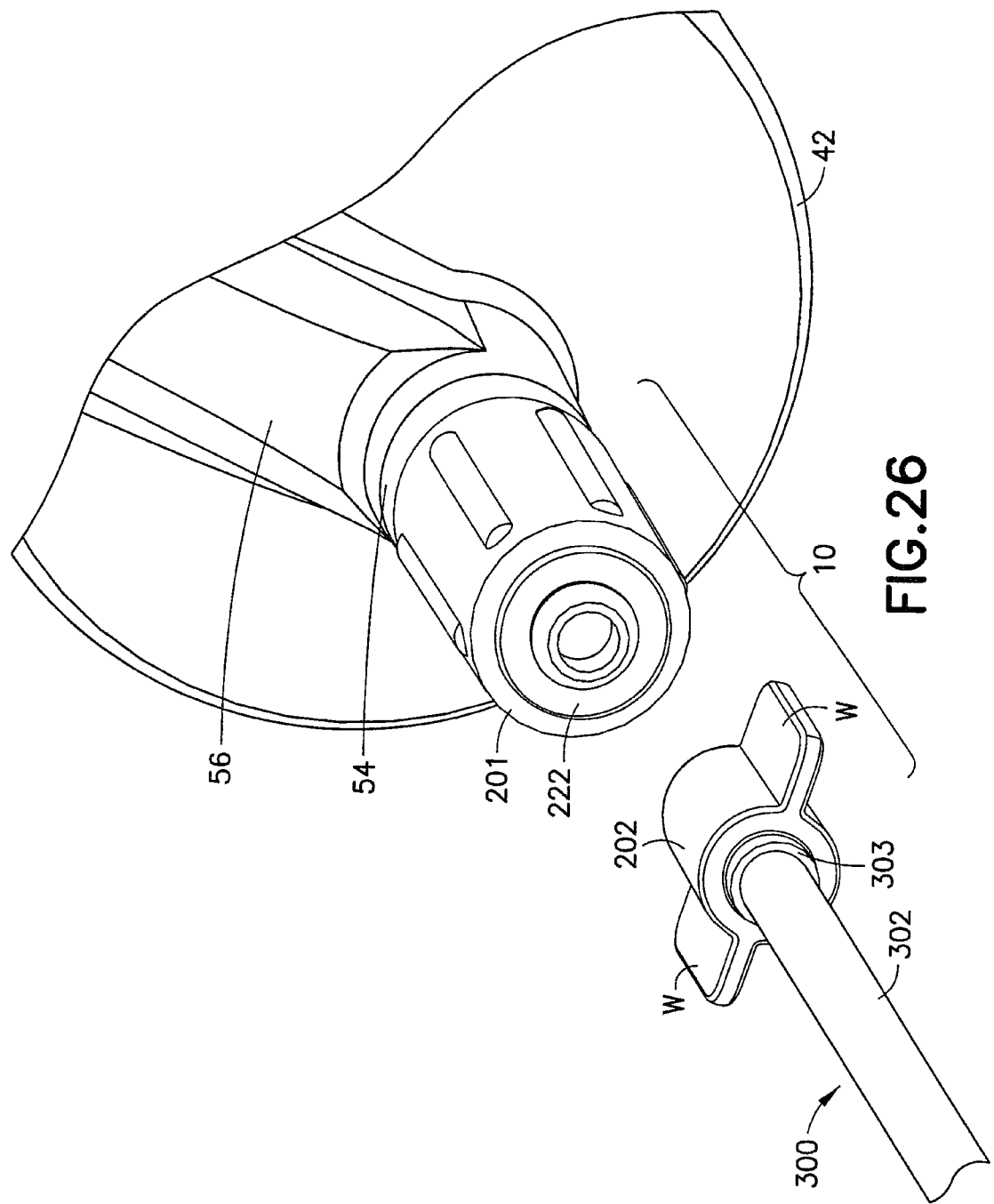
FIG. 26 is an exploded perspective view showing the single-use connector assembly of the medical connector assembly of FIG. 22 in a disconnected state.
Figure 27:
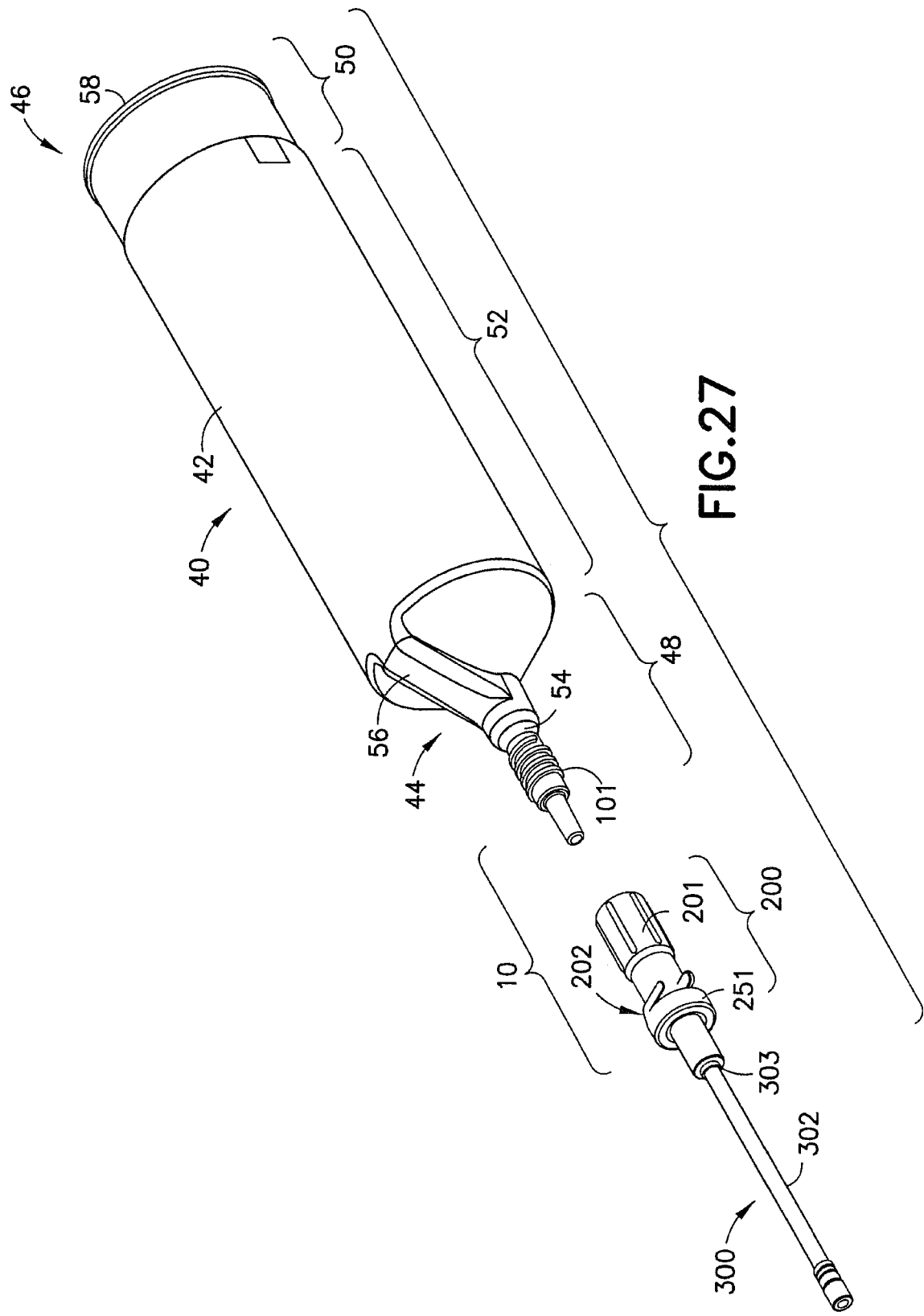
FIG. 27 is an exploded perspective view of another embodiment of the medical connector assembly in which a slidable connection may be provided as part of the single-use connector assembly.
Figure 28:
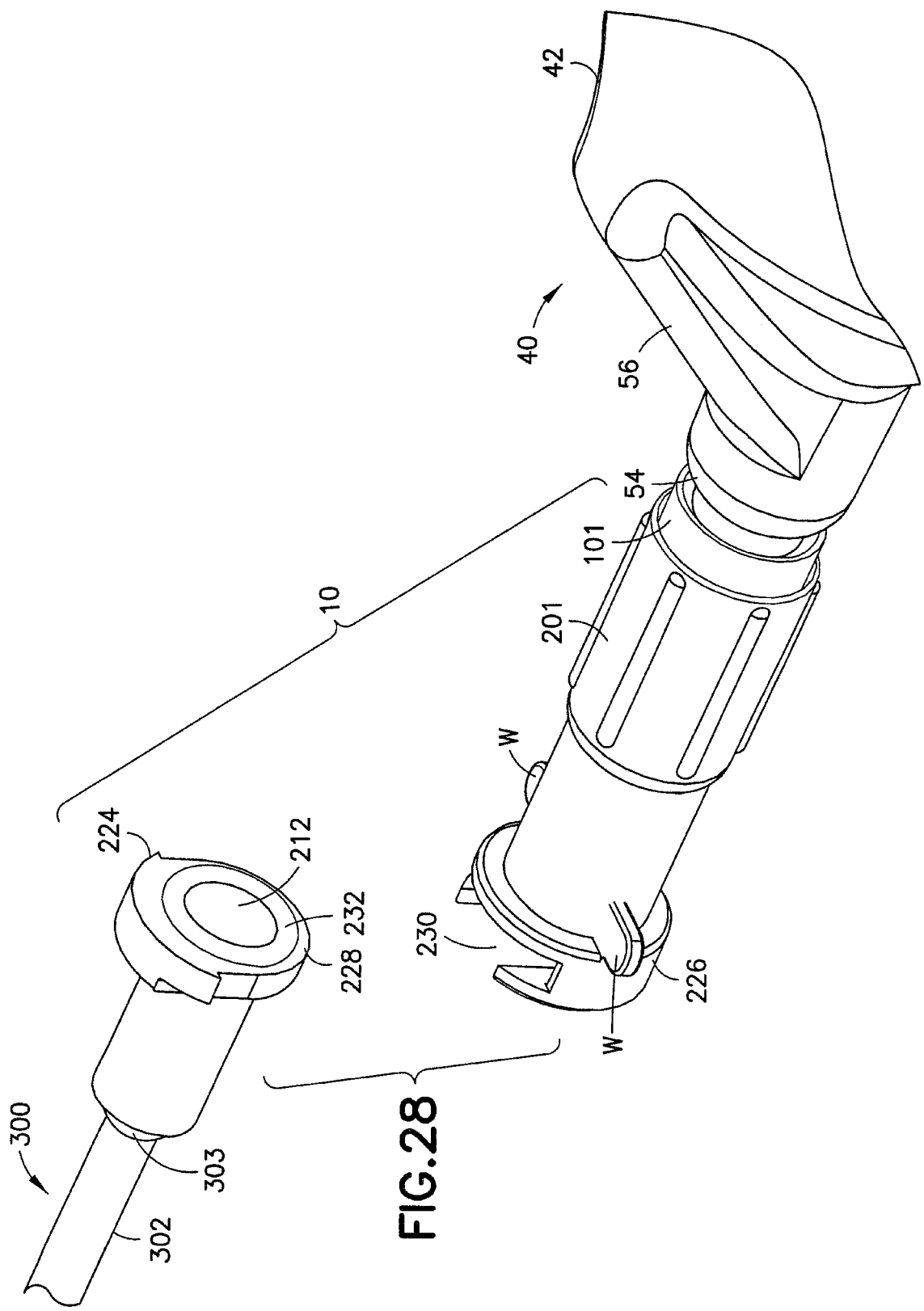
FIG. 28 is an exploded perspective view of the single-use connector assembly used in the medical connector assembly of FIG. 27 shown in a disconnected state.
Figure 29:
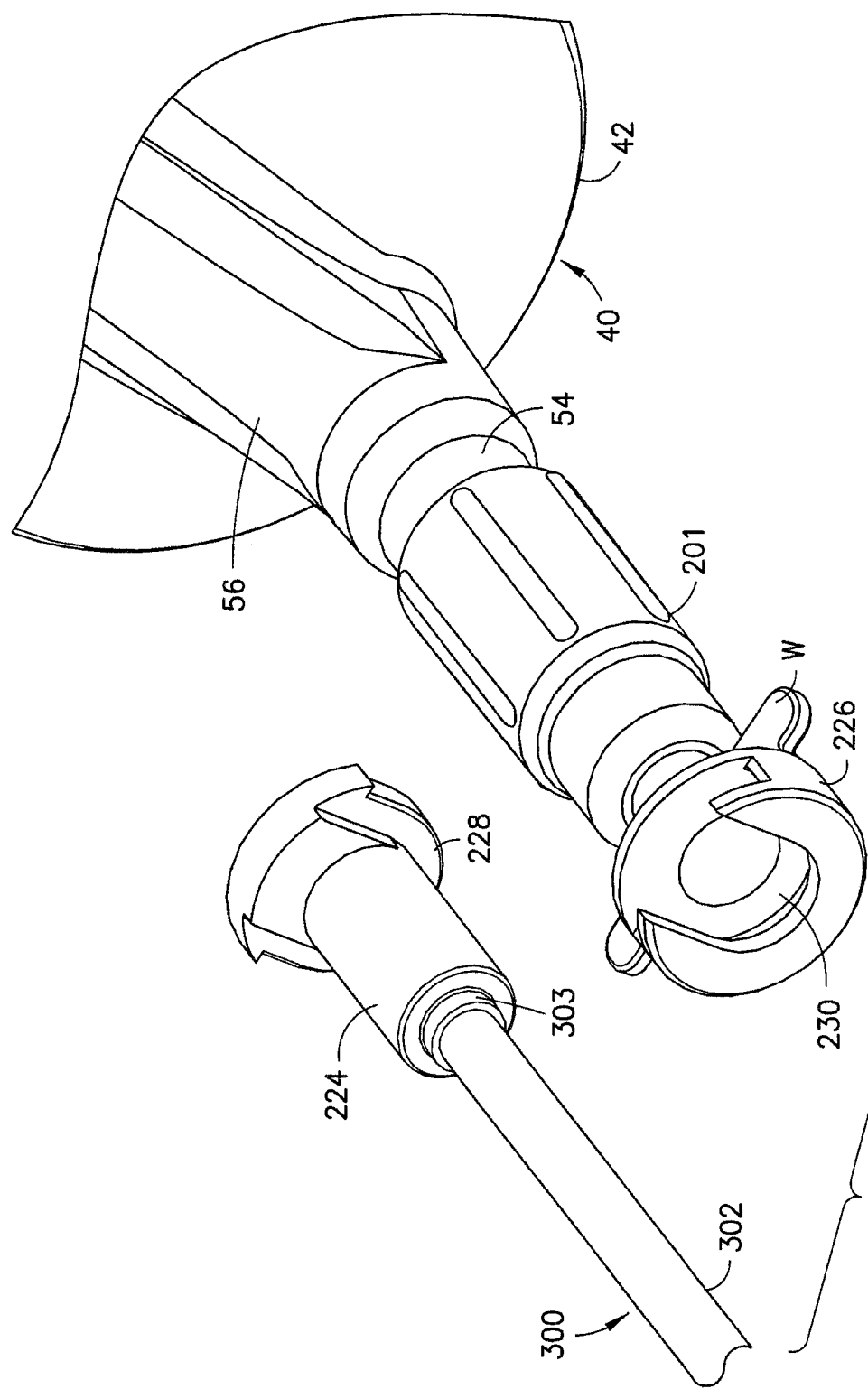
FIG. 29 is another exploded perspective view of the single-use connector assembly used in the medical connector assembly of FIG. 27 shown in a disconnected state.
Figure 30:
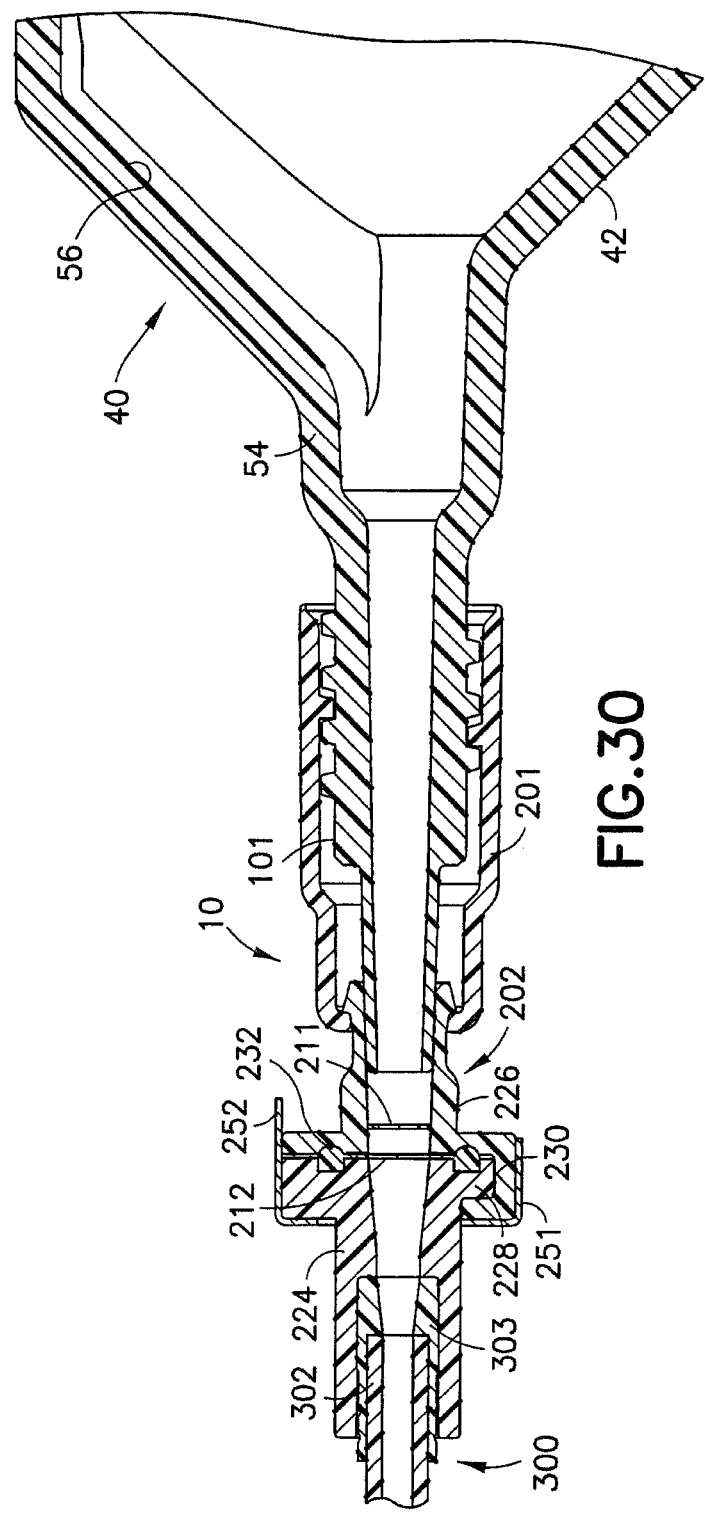
FIG. 30 is a longitudinal cross-sectional view of the medical connector assembly of FIG. 27.

Referring next to FIG. 16, another embodiment of the connector assembly 10 is shown and generally includes the multi-use connector assembly 100 and the single-use connector assembly 200 as described previously, but now the connector assembly 10 exhibits a multiple port configuration. In this embodiment, as in previous embodiments, the single-use connector assembly 200 includes multiple single-use connectors 201, 202 as described previously, but now the single-use connector assembly 200 shown in FIG. 16 is provided as a branch from a port on the multi-use connector assembly 100. The presently illustrated multi-use connector assembly 100 further comprises an additional, sterile multi-use connector 101' with an attached cap 110'. Once the cap 110' is removed, another single-use connector assembly 200 (not shown) may be joined to the multi-use connector assembly 100 at the multi-use connector 101', resulting in the multi-ported connector assembly 10. Upon connection of the multi-use connector assembly 100 and the branch single-use connector assembly 200 shown in FIG. 16, fluid can flow through the branch single-use connectors 201, 202 as desired. When the branch single-use connector 202 is removed, the anti-drip or anti-reflux flow control element 211 in the single-use connector 201 seals the fluid path against any fluid flow at normal operational pressure, in the same manner as described previously. The establishment of a second fluid connection is available through another single-use connector assembly 200 (not shown) added to the multi-use connector 101', which is accessed by removing dust cap 110'. As illustrated in this embodiment, the fluid path through the connector assembly 10 need not be linear or coaxial, and can be of any geometry that one skilled in the art finds advantageous in their particular situation. Likewise, connector attachment and separations can utilize various geometries.

In the discussion hereinafter, various embodiments of the connector assembly 10 are described that draw on the elements and features described hereinabove in this disclosure, or are common from one embodiment to the next. As such, for brevity and clarity, the following embodiment descriptions do not recite or describe elements or features that have been previously discussed elsewhere in this disclosure. In the following embodiments, a generic fluid path element 300 comprising tubing 302 with an overmolded filler piece 303 is shown in the views of the respective views for exemplary purposes.

Referring to FIGS. 17-21, an embodiment of the connector assembly 10 is shown that is suited for high pressure applications such as angiography using an angiographic syringe 40. A suitable high pressure syringe 40 adapted to interface with a power injector may be found in United States Patent Application Publication No. 2009/0216192 to Schriver et al., incorporated herein by reference for teachings related to the high pressure syringe 40. The high pressure syringe 40 generally comprises an elongated, cylindrical syringe body 42 having a front or distal end 44 and a rear or proximal end 46. The syringe body 42 generally defines an injection section 48 at the distal end 44 and an expansion section 50 at the proximal end 46. A generally cylindrical center or working section 52 of the syringe body 42 connects the injection section 48 and the expansion section 50. The center or working section 52 has a relatively uniform outer diameter. The injection section 48 tapers to form an elongated discharge neck 54. The injection section 48 and discharge neck 54 generally form the discharge outlet of the syringe 40. The expansion section 50 accommodates a syringe plunger (not shown). The injection section 48 is formed with a hollow alignment flange or tab 56 for orienting and aligning the syringe 40 in the power injector. Additionally, the proximal end 46 of the syringe body 42 defines an outward extending radial lip 58. The radial lip 58 is adapted to engage or contact an electrical contact switch in the power injector to activate the electrical switch to identify when the syringe 40 is properly loaded in the power injector. The radial lip 58 preferably has an outer diameter that is no greater than the outer diameter of the center or working section 52 of the syringe body 42 so that the syringe 40 may be smoothly accepted into a pressure jacket (not shown) associated with the power injector during a syringe-loading procedure.

In this embodiment, after removing caps 110, 210, described previously, the single-use connector assembly 200 is threaded onto the multi-use connector 101, provided on the discharge neck 54 of the syringe 40 or formed integrally as part of the discharge neck 54 as shown, using, for example, a right-hand threaded engagement and is ready for use. The sheath 251 surrounds the single-use connector assembly 200 and has a circumferential notch or serrated connection 251n that separates the first sheath element 251a from the second sheath element 251b. The seal between the single-use connectors 201, 202 occurs at elastomeric flow control elements 211, 212. The force maintaining the seal between the single-use connectors 201, 202 against the pressure of injection can be created by joining the single-use connectors 201, 202 during or after manufacture and/or by having the sheath 251 lock over the collar 60, or by having threads, bayonet fittings, or other mechanical connections (not shown) between the sheath 251 and the single-use connector 201. The single-use connector 201 is able to withstand the axial fluid pressure during operation of the syringe 40 by having right-handed threads between the multi-use connector 101 and the single-use connector 201. The single-use connector 201, in this example, is comprised of two (2) connector elements 201x and 201y fitted together by a barbed connection or another suitable connection arrangement. In the present embodiment, the first sheath element 251a is a ratchet that prevents disengagement of the right-handed threads when engaged with a collar 60 on the discharge neck 54 of the syringe 40. In use, when a user is ready to unthread the single-use connector assembly 200, the sheath 251 separates at circumferential notch 251n, leaving the single-use connector 201 behind as a sterility retaining cap. As mentioned previously, restraint against axially-directed forces or loads can be further enhanced by optionally having tabs 251x formed as part of first sheath element 251a that engage a collar 60 on the discharge neck 54 of the syringe 40. The second sheath element 251b can be removed in the process of or after unthreading the single-use connector 201, so that a new single-use connector assembly 200 can be attached for the next use.

Referring next to FIGS. 22-26, a frangible connection may be provided as part of the single-use connector assembly 200. As in the immediately foregoing embodiment, the multi-use connector 101 is provided on the discharge neck 54 of the syringe 40 or formed integrally as part of the discharge neck 54 as shown. In this embodiment, the single-use connector 202 is rotatably connected to the opposing single-use connector 201. Additionally, the single-use connector 202 is adapted to break apart along a thinned section 220 (e.g., a circumferential notch) such that, upon breaking, a portion 222 of the single-use connector 202 may be said to be retained with the opposing single-use connector 201. The opposing single-use connector 201 is formed as a sheath part that is in threaded engagement with the multi-use connector 101. In the discussion of this and other embodiments described herein, it may be considered that the single-use connector 202 ends at the break point, and the single-use connector 201 is comprised of several physical parts, one of which is the segment that remains behind after breaking at thinned section 220. This illustrates the principle that individually identified fluid elements can be assembled from discrete physical parts, or complimentarily, a single physical part may serve or function as part or all of one or more individually identified or discussed fluid path elements. Or, said another way, the key aspects or functions of the various fluid path elements may be achieved with one or more than one physical part or as part of a physical part.

In use, the single-use connector assembly 200 comprising connectors 201, 202 is threaded onto the multi-use connector 101 on the discharge neck 54 of the syringe 40, and the syringe 40 is then ready for use. To disconnect, the user grasps wings W on the single-use connector 202 and twists. This rotational motion breaks the thinned section 220, physically separating portion 222 from the main body of the single-use connector 202, and the separated portion 222 is retained with the opposing single-use connector 201, which associated with the multi-use connector 101. In the present embodiment where a frangible element is used, it is desirable for a power injector associated with the syringe 40 or other associated equipment to have a strain relief notch, latch, or cover to prevent inadvertent disconnection.

Referring next to FIGS. 27-30, the single-use connector assembly 200 may exhibit a sliding connection between elements. As in the immediately foregoing embodiments, the multi-use connector 101 is provided on the discharge neck 54 of the syringe 40 or formed integrally as part of the discharge neck 54 as shown. The single-use connector 202, in this example, is comprised of two (2) sliding connector elements 224, 226. The first connector element 224 comprises a depending portion 228 adapted to fit within a mating receptacle 230 defined in the opposing connector element 226 of the single-use connector 202. The second connector element 226 is secured to the opposing single-use connector 201 by a barbed connection or another suitable connection arrangement, as described previously in connection with FIGS. 17-21. In this embodiment, the flow control element 212 in the receiving connector element 226 of the single-use connector 202 incorporates a raised area 232 to seal to a mating surface of the opposing the flow control element 211 in the sliding connector element 224. In this embodiment, the sheath 251 may be in the form of heat shrink wrapping with a tab 252 having serrations (not shown) to assist in removal of the sheath 251. The sheath 251 discourages accidental disconnection of the single-use connector 202. Once the sheath 251 is removed, the connector elements 224, 226 of the single-use connector 202 can be detached from one another, and the connector element 224 and the tubing 302 of the fluid path element 300 connected thereto can be discarded.

Figure 31:
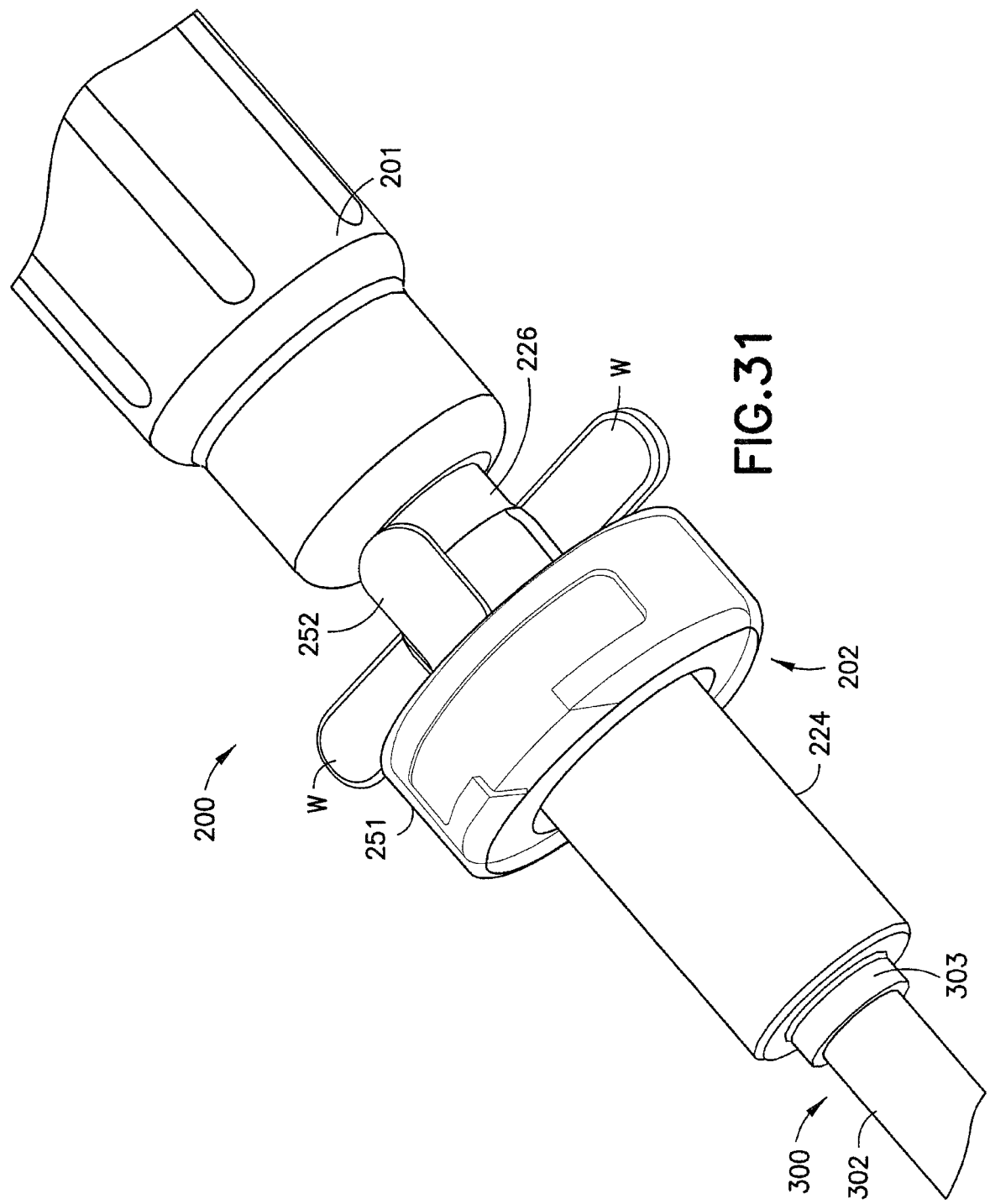
FIG. 31 is a perspective view of a modification of the single-use connector assembly shown in FIGS. 27-30.
Figure 32:
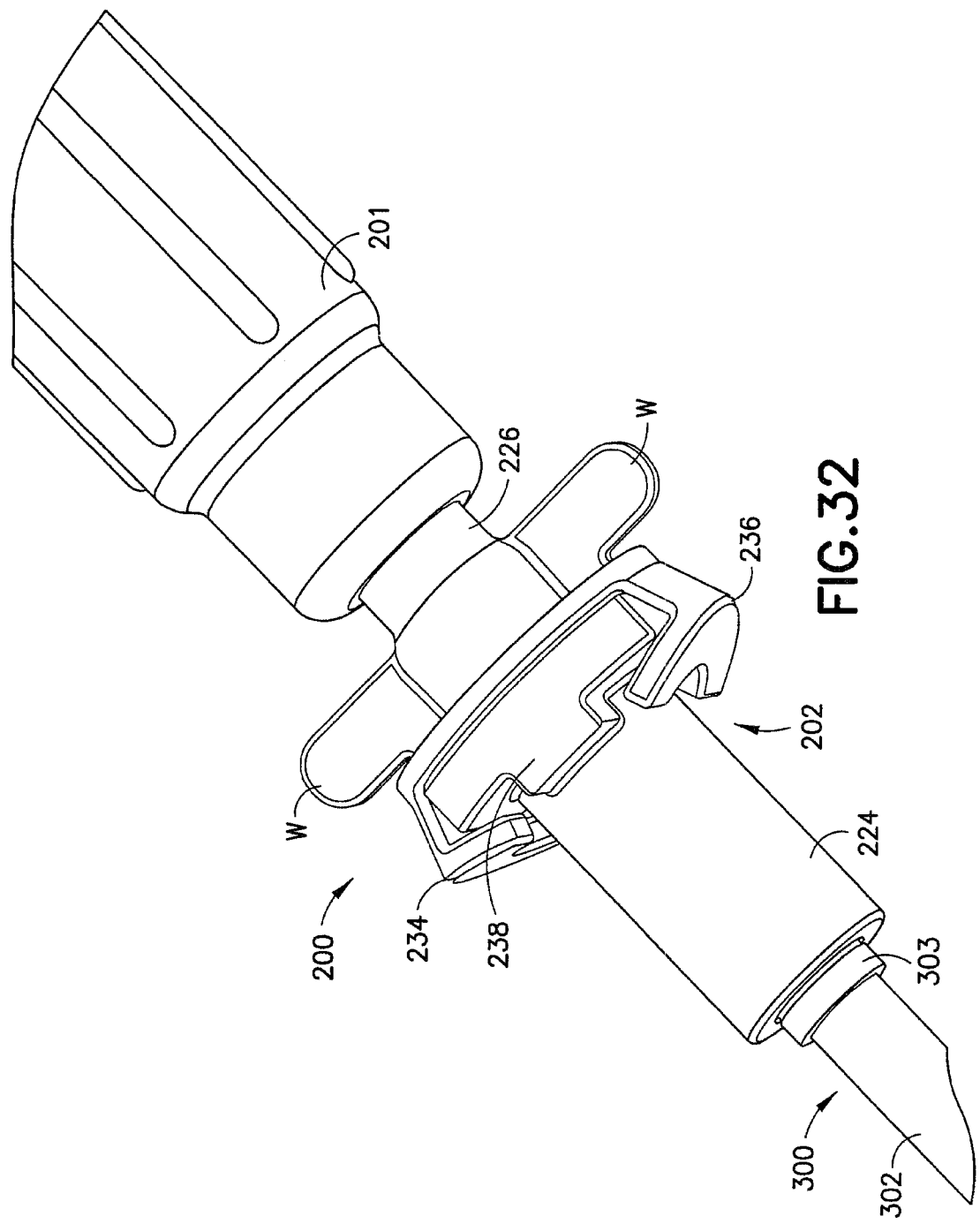
FIG. 32 is a perspective view of the single-use connector assembly shown in FIG. 31 with a shrink-wrap sheath element removed.
Figure 33:
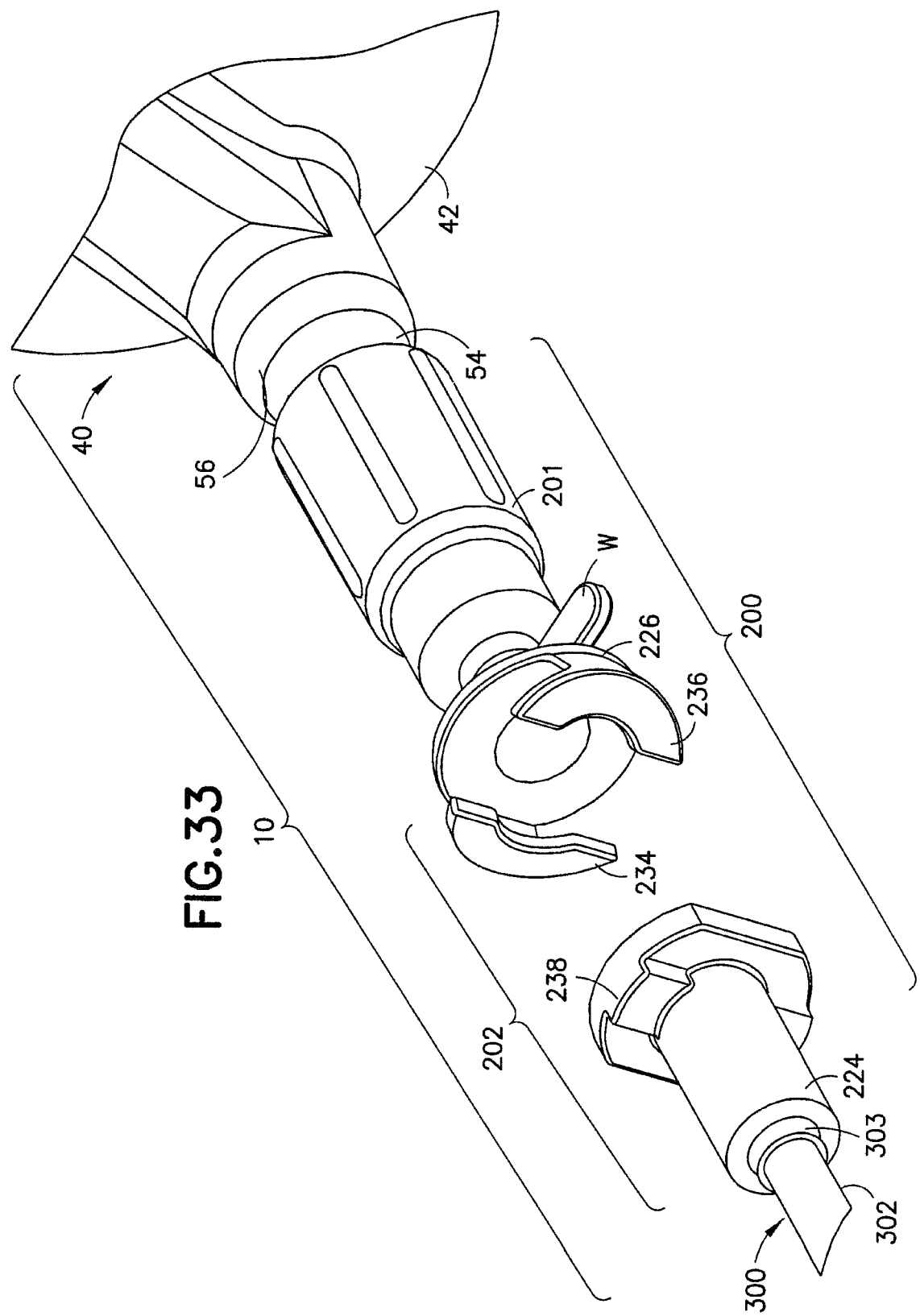
FIG. 33 is an exploded perspective view of the single-use connector assembly FIG. 31.

Referring to FIGS. 31-33, a modification of the single-use connector assembly 200 of FIGS. 27-30 is shown. In this embodiment, the second connector element 226 of the single-use connector 202 has two (2) folding elements 234, 236 that fold over an end or head portion 238 of the first connector element 224 to hold the single-use connector 202 together and in a position mated with the single-use connector 201. The frangible sheath 251 holds the folding elements 234, 236 in place and secures the connection. When the frangible sheath 251 is removed, the folding elements 234, 236 separate and cannot maintain the connection between the single-use connectors 201, 202. The folding elements 224, 226 may be formed to be biased apart from one another. This embodiment has an additional benefit of not being easily or accidentally reconnected.

Figure 34:
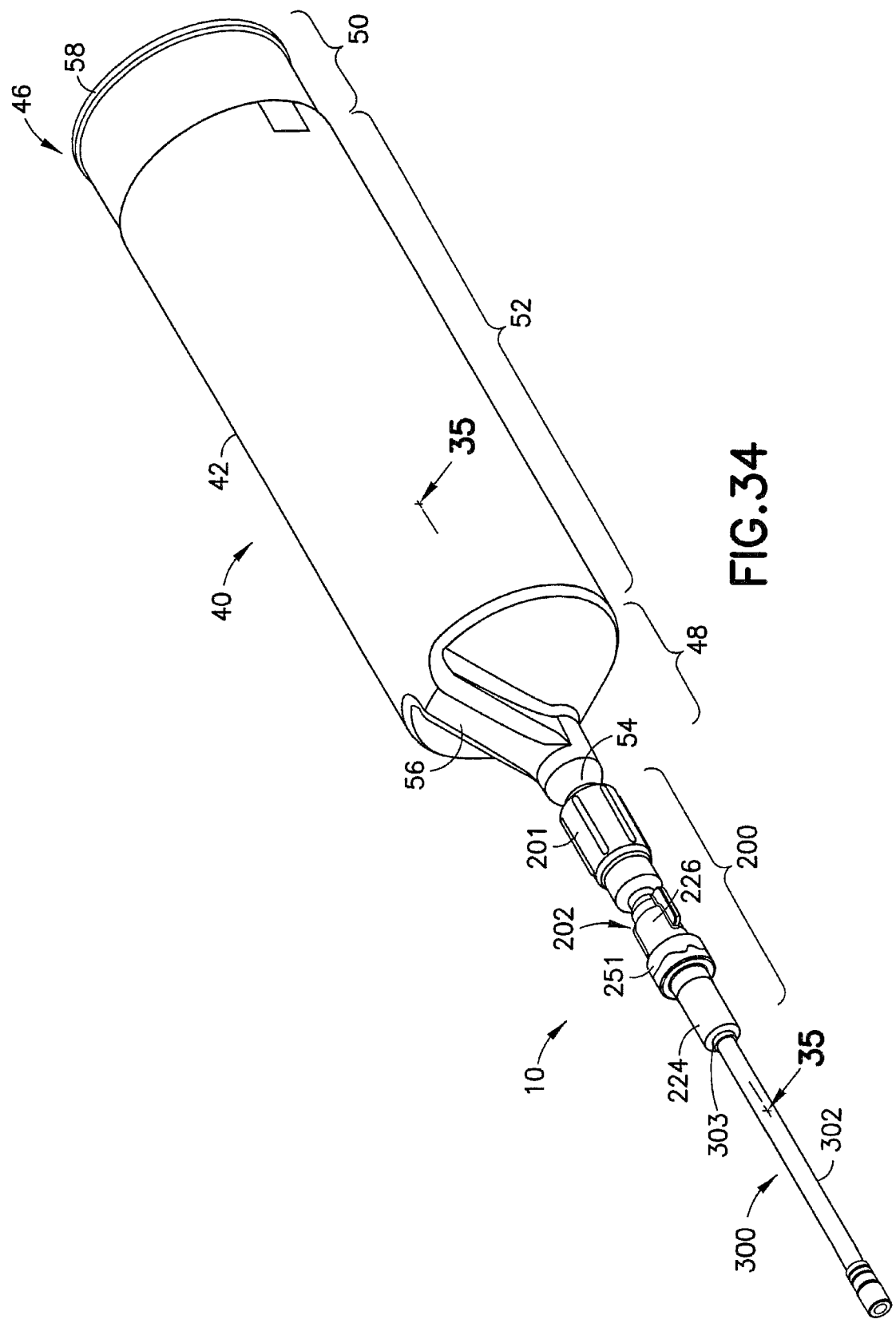
FIG. 34 is an exploded perspective view of another embodiment of the medical connector assembly in which a fluid connection may be maintained by a shrink wrap sheath element.
Figure 35:
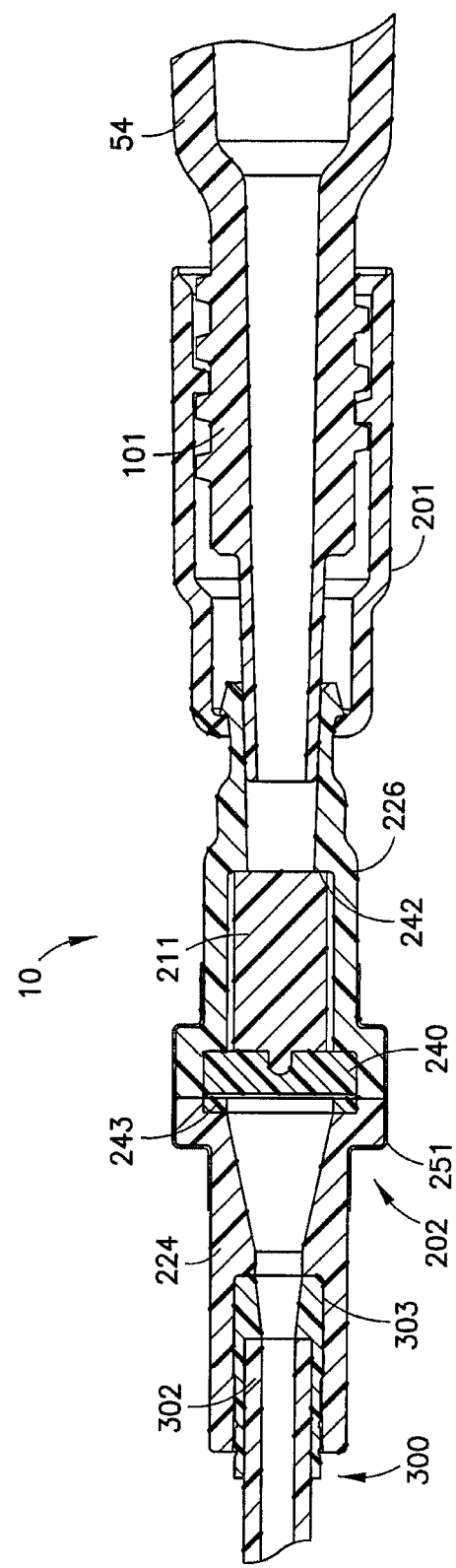
FIG. 35 is a longitudinal cross-sectional view of the medical connector assembly of FIG. 34.

In FIGS. 34-35, a further modification of the single-use connector assembly 200 of FIGS. 27-30 is shown. In this embodiment, the first and second connector elements 224, 226 of the single-use connector 202 are in abutting engagement and held together by the frangible shrink wrap sheath 251 alone, which secures their connection. When the frangible sheath 251 is removed by pulling pull tab 252 or gripping and snapping the single-use connector 202 to tear the frangible sheath 251, the first and second connector elements 224, 226 separate from one another. FIGS. 34-35 also show an alternative embodiment for the internal flow control element 211. The flow control element 211 may be in the form of an elastomeric solid cylinder disposed between an annular element 240 provided between the first and second connector elements 224, 226 and an internal shoulder 242 defined in the connector element 226. When there is no pressure across the cylinder flow control element 211, the cylinder flow control element 211 seals against the internal shoulder 242. When pressure on the right side of the cylinder flow control element 211 (as shown in FIG. 35) is greater than pressure on the left side, the cylinder flow control element 211 is compressed slightly and fluid can flow. A seal 243 having some adhesion to the parts abutting it may be provided to augment the strength of the connection between the first and second connector elements 224, 226.

Figure 36:
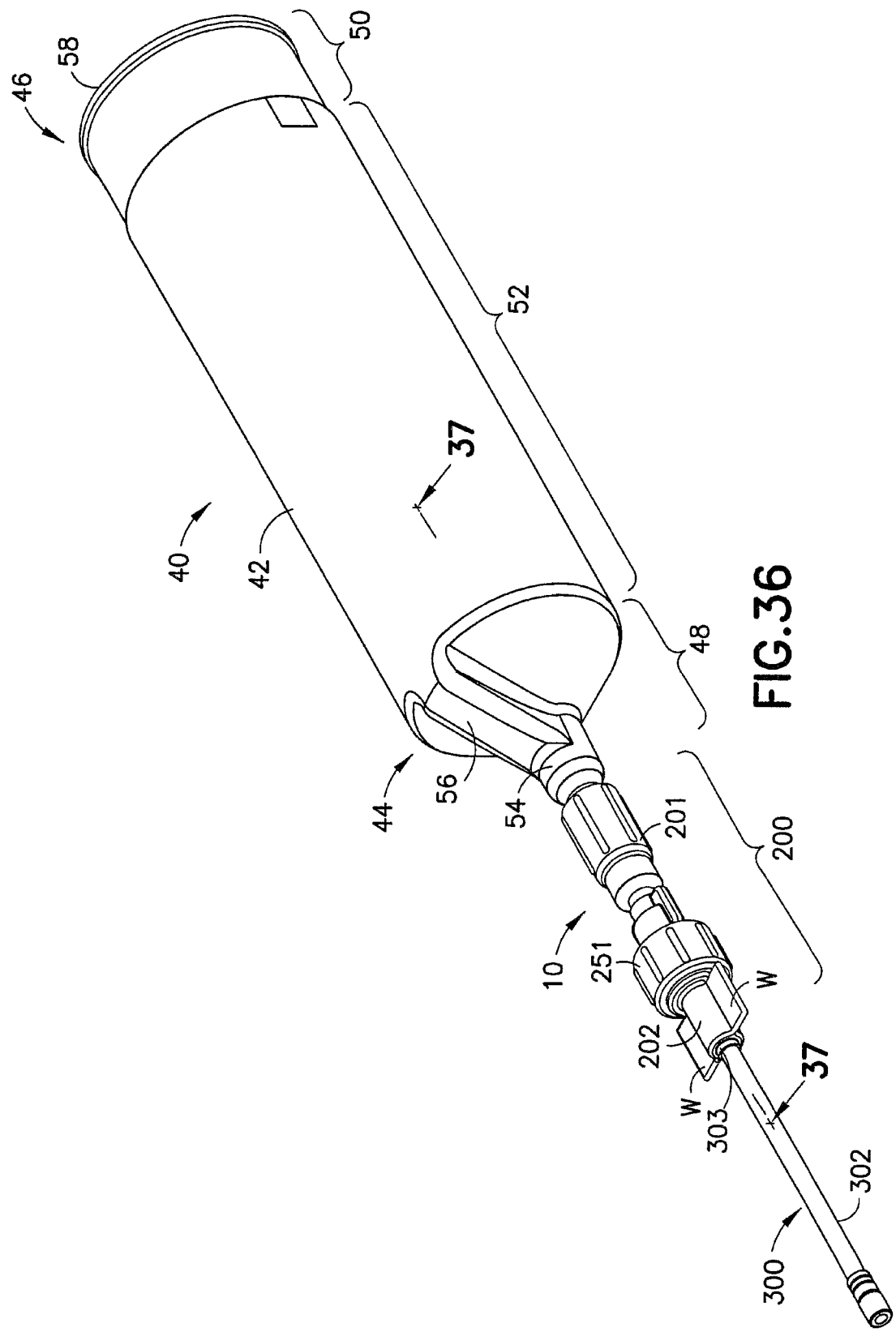
FIG. 36 is a perspective view of another embodiment of the medical connector assembly associated with an angiographic syringe.
Figure 37:
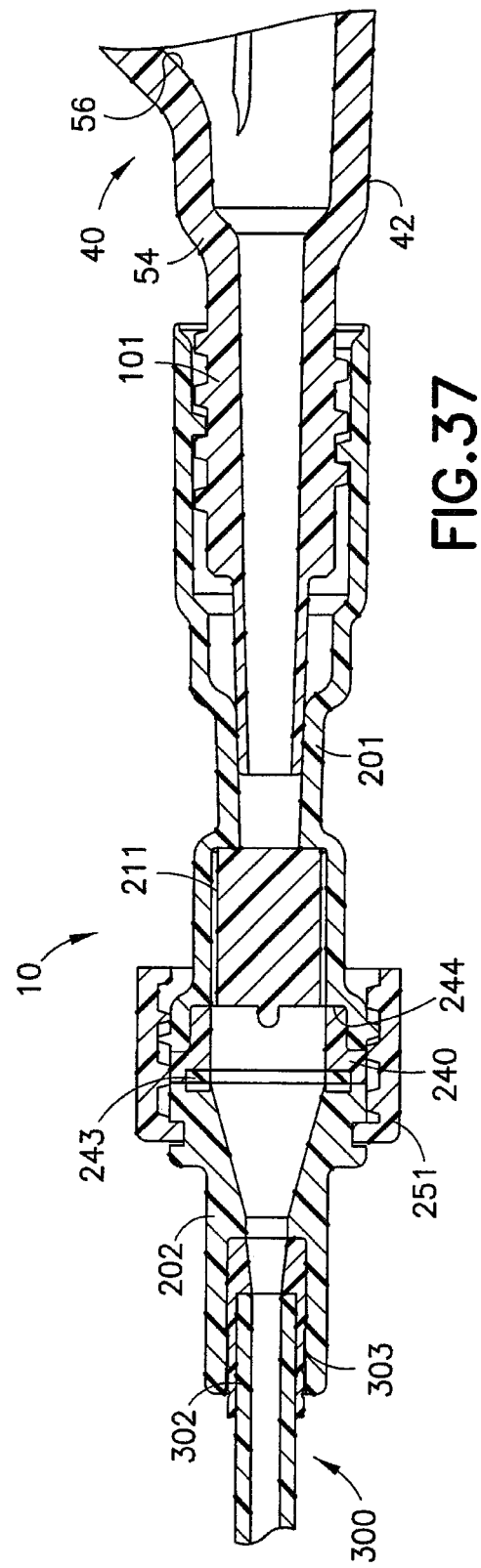
FIG. 37 is a cross-sectional view taken along line 37-37 in FIG. 36.
Figure 41:
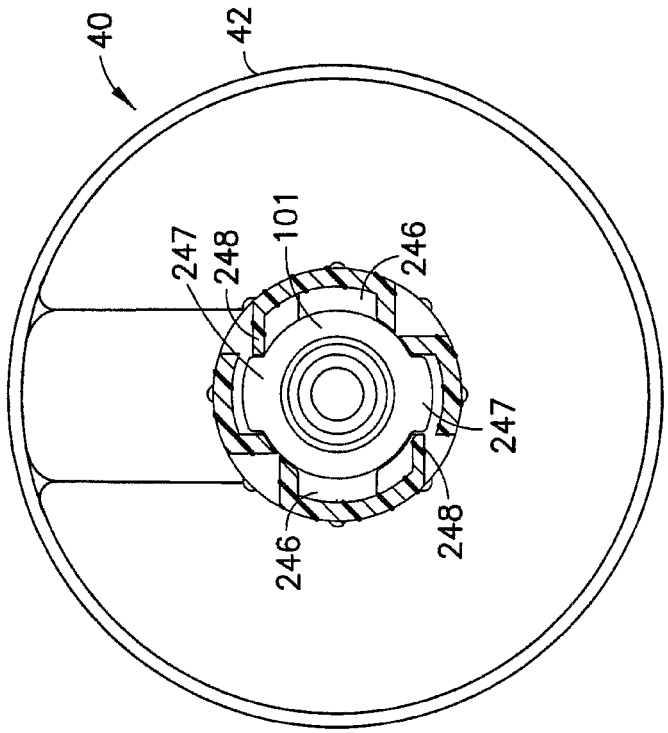
FIG. 41 is an end view showing the engaged and locked state of the medical connector assembly and syringe as shown in FIG. 40.
Figure 39:
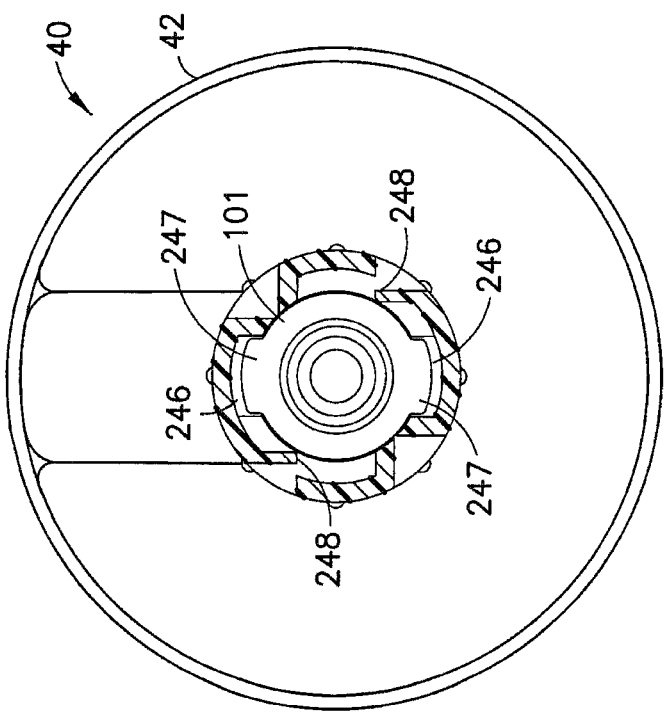
FIG. 39 is an end view showing an engaged state of the medical connector assembly and syringe of FIG. 36.
Figure 40:
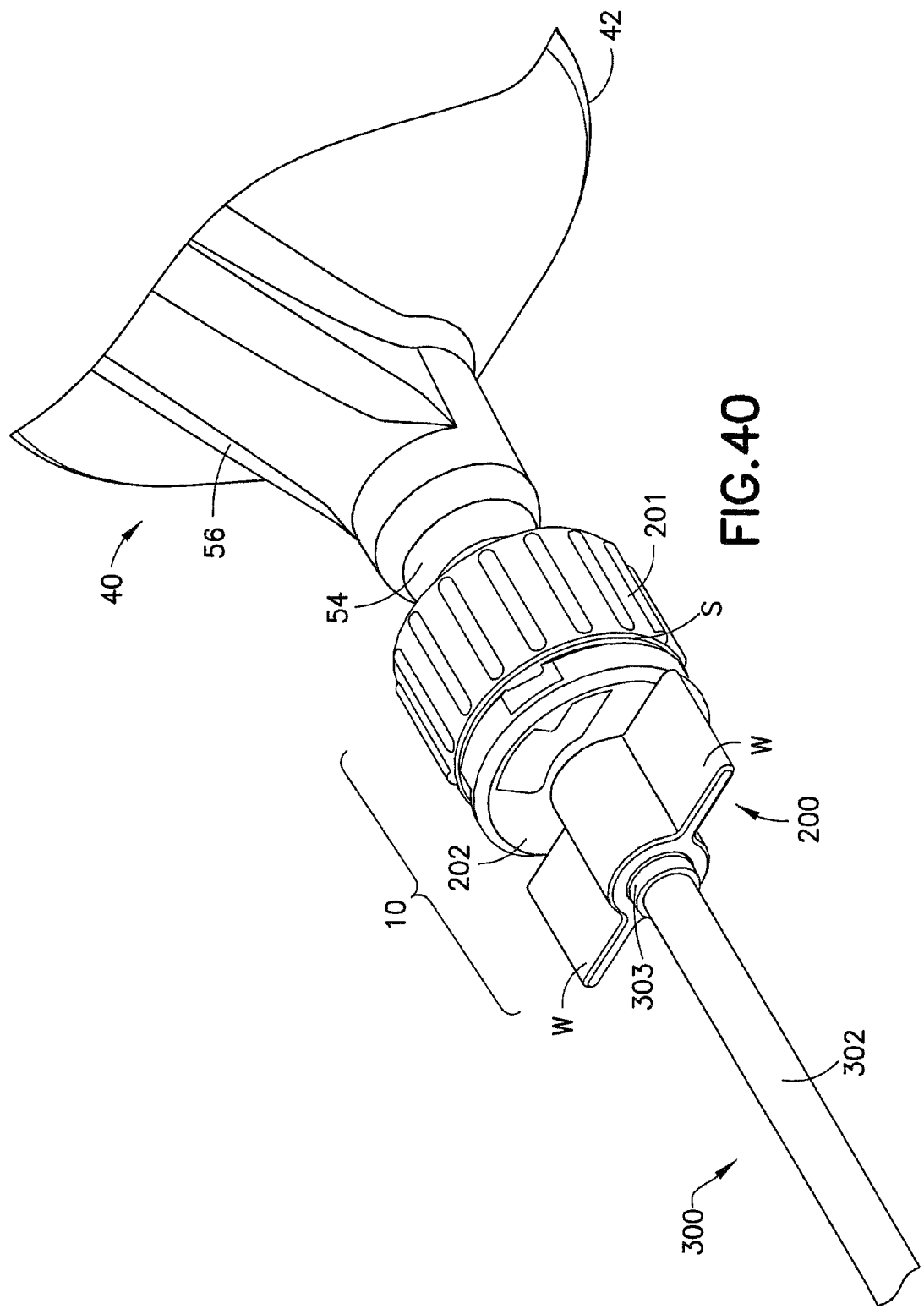
FIG. 40 is a perspective view showing an engaged and locked state of the medical connector assembly and syringe of FIG. 36.
Figure 42:
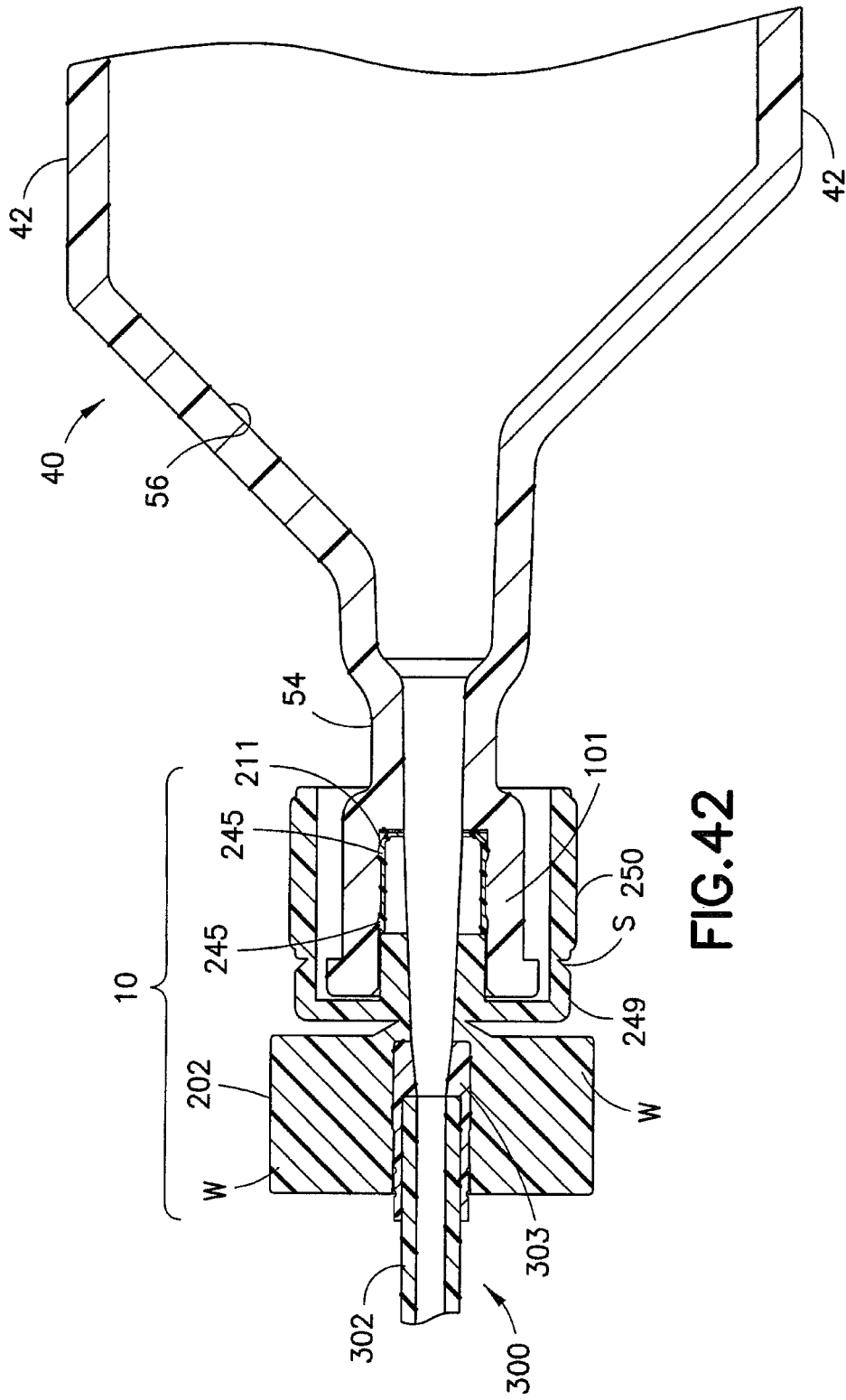
FIG. 42 is a cross-sectional view showing the engagement of the medical connector assembly and syringe of FIG. 36.

In FIGS. 36-37, another embodiment of the single-use connector assembly 200 is shown. In this embodiment the sheath 251, which is non-frangible in this embodiment, is adapted for a threaded connection to the single-use connector 201 via, for example, left-handed (e.g., counterclockwise-operated) threads. The sheath 251 provides the holding force to hold and seal the single-use connector 202 to the single-use connector 201. The single-use connector 201 is adapted for threaded engagement with the discharge neck 54 of the syringe 40 via, for example, right-handed (e.g., clockwise-operated) threads. In use, after removing the respective dust caps 110, 210 (discussed previously), the single-use connector 201 is threaded onto the multi-use connector 101 provided on the discharge neck 54 of the syringe 40 or formed integrally with the discharge neck 54 using the right-handed threaded engagement. Thus, the single-use connector 201 is placed in engagement with the multi-use connector 101 on the discharge neck 54 of the syringe 40 by rotating the single-use connector 201 clockwise. After use, to separate the single-use connector 202 from the opposing single-use connector 201, the sheath 251 is held and rotated clockwise to release the engagement owing to the left-handed threaded engagement. By providing the foregoing left-handed/right-handed threaded engagements, the risk of removing the connection between the single-use connector 201 and the multi-use connector 101 on the discharge neck 54 of the syringe 40 can be reduced and potentially eliminated. As will be apparent to those skilled in the art, the foregoing left-handed/right-handed threaded engagements may be reversed. As an alternative, the foregoing left-handed/right-handed threaded engagements may be replaced by similar left-handed/right-handed bayonet connections or other equivalent securing methods may be used. The embodiment shown in FIGS. 36-37 utilizes a similar cylinder flow control element 211 as shown in FIG. 35, but the annular element 240 is now provided axially between the opposing single-use connectors 201, 202 and abuts an internal shoulder 244 defined in single-use connector 201.

Referring to FIGS. 38-42, for simplicity of manufacture and reduced cost, the single-use connectors 201, 202 may be manufactured from a single piece of plastic. In this embodiment, the flow control element 211 may also be a single plastic piece, but now adapted to fit onto the end of the single-use connector 201 in an analogous manner to a water bottle cap. The flow control element 211 is preferably elastic and may incorporate bulges or rings 245 that seal against the inner surface of the multi-use connector 101, which may again be provided on the discharge neck 54 of the syringe 40 or formed integrally as part of the discharge neck 54. In this embodiment, tubing 302, which forms part of the fluid path element 300, may be bonded to the single-use connector 202, optionally with a filler piece 303, which is also shown in connection with tubing 302, as shown in previous figures as well. To optimize assembly via, for example, two-shot molding or overmolding processes, the lumen through the single-use connectors 201, 202 can be straight or tapered to accommodate a core pin to support the molding of flow control element 211 onto the single-use connector 201.

In use, the single-use connector 201 may be formed with bayonet slots 246 that may be engaged with mating bayonet tabs 247 on the multi-use connector 101 provided on the discharge neck 54 of the syringe 40. This engagement may be secured by rotating on or the other of the single-use connector 201 and syringe 40 by 90°. Flexing elements 248 are provided on the single-use connector 201 to prevent the reversal of this bayonet connection once engaged. Fluid can now be transmitted through the connector assembly 10. To remove the single-use connector 202 from the opposing single-use connector 201, wings W on the single-use connector 202 are held and twisted. Because of the locking of the bayonet connection, they can be twisted in either direction. To remove the single-use connector 201 for installation of a new single-use connector assembly 200 after the single-use connector 201 has been used as a sterile cap, the single-use connector 201 may be gripped and twisted to break the single-use connector 201 along a weakened section or score line S (e.g., a circumferential notch) into two elements, a cap element 249 and a ring element 250. The cap element or part 249 can be removed and the multi-use connector 101 is again ready for use. The ring element or part 250 may remain in place. After each use, another ring element 250 accumulates. By choosing the size of the ring element 250 and the length of the fluid path element on which they accumulate, such as on the discharge neck 54 of the syringe 40, the accumulation of ring elements 250 can be used to physically limit the number of times that the syringe 40 and/or multi-use connector 101 is utilized, for the sake of sterility, safety, reliability, etc. Alternatively, tabs, score lines, and other similar features (not shown) may be provided to allow the user to break the ring elements 250 for removal after connection of a new single-use connector assembly 200. Optionally, the multi-use connector 101 may incorporate a feature such as a wedge or edge (not shown) that automatically splits the ring elements 250 as they are pushed away from the multi-use connector 101 so that the ring elements 250 fall from the fluid path or can subsequently be removed by the user.

The above-described connector assembly 10 may be applied to a variety of existing medical systems. For example, the various fluid elements shown in U.S. Pat. Nos. 5,806,519, 5,840,026; 5,739,508; 5,569,181 and 5,843,037, all of which are fully incorporated herein by reference, may be used with any of the features described hereinabove. In the connection steps described previously, a sterile airflow may be desirable during the action of uncapping of connectors and/or connecting the first single-use connector 201 to the multi-use connector 101. However, it should understood that, according to this disclosure, sterile air need not be flowing during disconnection of the first single-use connector 201 in any of the foregoing embodiments because the first and second single-use connectors 201, 202 serve as sterility retaining "caps" for their respective fluid path segments, and the use of sterile air is provided to enhance sterility.

Much of the foregoing discussion has centered upon the fluid supply side of a fluid delivery system. However, the various embodiments described hereinabove may be applied to the patient side where there is often a need for multiple fluid lines for delivery or withdrawal of fluids and which must be connected sequentially to a patient access device over the time of their treatment. The embodiments described hereinabove may be applied to patient side of a fluid delivery to improve sterility through these multiple connections to a patient access device. In addition, as an example, the internal flow control elements 211, 212 provide additional benefits by reducing the likelihood that blood will inadvertently leak from the patient access device. In practical application, the internal flow control elements 211 and 212 desirably tightly abut one another so that no blood or bodily fluid is trapped therebetween for subsequent release when the two (2) single-use connectors 201, 202 are separated.

The exemplary embodiments described hereinabove are all generally directed to a plurality of single-use connectors 201, 202 which form a fluid path or fluid path element to or from a multi-use connector 101, wherein removal of one or more of the single-use connectors 201, 202, optionally with additional fluid path elements, leaves at least one single-use connector 201, 202 as protection on the multi-use connector 101.

Figure 43:
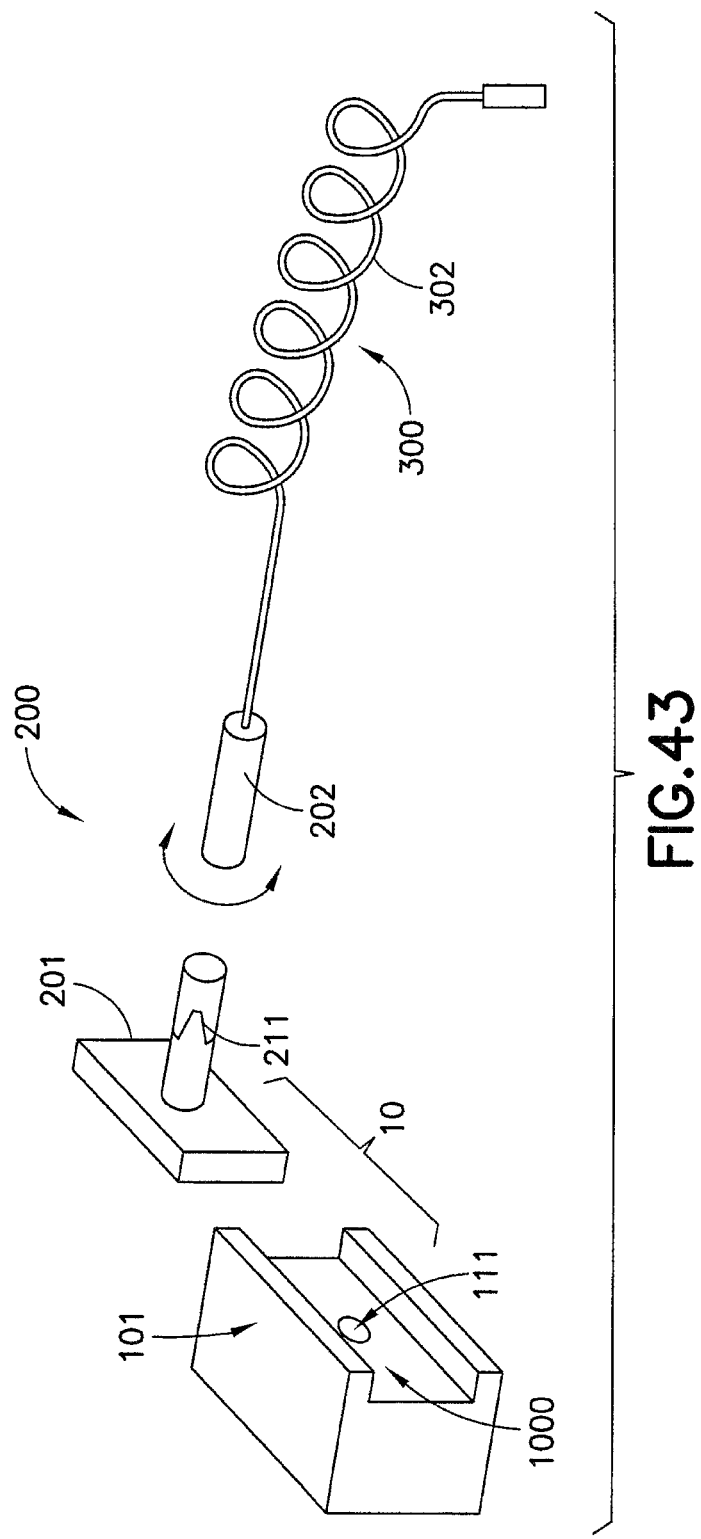
FIG. 43 is a schematic perspective view of another embodiment of the medical connector assembly exhibiting a sliding connection between the single-use connector assembly and the multi-use connector assembly.

Lastly, referring to FIG. 43, an embodiment is shown in which the connection between the multi-use connector assembly 100 and the single-use connector assembly 200 is made by sliding the single-use connector 201 into a slot 1000 to hold it in place in relation to multi-use connector 101. The slot 1000 may be part of the multi-use connector 101 or the multi-use connector 101 may be attached to or integrated as part of an apparatus, such as a fluid pump device. When the single-use connector 201 is properly positioned, the flow control element 111 mates with the opposing flow control element 211 or the opposing single-use connector 201, to form a seal which prevents the leakage of fluid during use. As in previous embodiments, after use, the single-use connector 202 may be removed, for example by twisting or breaking, and the opposing single-use connector 201 remains in place to retain the sterility of the multi-use connector 101. Optionally, single-use connector 201 and/or slot 1000 may have ratchets, ramps, or other mechanical or electrical means such that sliding can only occur in one direction. Also optionally, the connection may be configured such that the only way to remove the single-use connector 201 is by dislodging the single-use connector 201 from the slot 200 by using a new single-use connector assembly 200. This embodiment has a benefit that there never is a time when the fluid control element 111 is open and accessible for accidental contact, even when removing the dust cap 110, or "used" connectors 201 serving as dust caps as described previously, which may be removed by application of the first single-use connector assembly 200 or a subsequent single-use connector 201 in a subsequent single-use connector assembly 200. In another variation, multiple sterile single-use connectors 201 may be prepackaged in a magazine which mates with the slot 1000 to provide for easy loading of new fluid paths. Also, if this embodiment is used with a catheter inserted into a patient, the fluid path element 300 (as well as the fluid path into the multi-use connector 101) can be parallel to the sliding element rather than perpendicular as show in this figure. This low profile arrangement, which is optionally curved or barrel-shaped, may make it much easier to tape to a patient's arm and a low profile connector reduces the possibility of inadvertent contact with unsterilized surfaces. Moreover, when used with a catheter, it is desirable to have sterilized caps 110 available that can be placed on the multi-use connector 101 when the patient is not connected to a fluid path element 300.

While several embodiments of a sterility retaining medical connector assembly and method for retaining sterility of a reusable portion of the medical connector assembly are shown in the accompanying figures and described hereinabove in detail, those skilled in the art may make modifications and alterations to these embodiments without departing from the scope and spirit of the invention. Accordingly, the foregoing description is intended to be illustrative rather than restrictive. The invention is defined by the appended claims and all changes to the invention that fall within the meaning and the range of equivalency of the claims are to be embraced within their scope

The invention claimed is:

1. A medical connector assembly, comprising:
a multi-use connector comprising a proximal end opposite a distal end along a longitudinal length thereof;
a removable cap adapted to cover the distal end of the multi-use connector;
a plurality of single-use connectors releasably connected to each other by a connecting arrangement in series to form a fluid path therethrough and each comprising a proximal end opposite a distal end along a longitudinal length thereof; and
a flow control element associated with each of the plurality of single-use connectors,
wherein the distal end of the multi-use connector is releasably connected to the proximal end of a first of the single-use connectors connected in series after removal of the removable cap from the distal end of the multi-use connector, and
wherein each flow control element is configured to prevent fluid flow through the fluid path until a sufficient fluid pressure difference across the flow control element is reached
wherein, when a most distal single-use connector of the single-use connectors connected in series is disconnected from a next most distal single-use connector, the next most distal single-use connector remains connected to the multi-use connector as a sterility retaining cover.

2. The medical connector assembly of claim 1, wherein the flow control element in the first of the single-use connectors connected in series is configured to prevent fluid flow when a second of the single-use connectors connected in series is disconnected from the first of the single-use connectors.

3. The medical connector assembly of claim 2, wherein each flow control element is configured to prevent fluid flow in either direction through the fluid path.

4. The medical connector assembly of claim 1, wherein at least one of the flow control elements is a one-way check valve.

5. The medical connector assembly of claim 1, wherein at least one of the flow control elements is a two-way check valve.

6. The medical connector assembly of claim 1, wherein at least one of the flow control elements is a slit diaphragm.

7. The medical connector assembly of claim 1, wherein at least one of the flow control elements is internal to the fluid path.

8. The medical connector assembly of claim 1, wherein the multi-use connector comprises a flow control element.

9. The medical connector assembly of claim 1, further comprising a sheath disposed over an exterior of the medical connector assembly to extend from the multi-use connector and continuing along the single-use connectors connected in series, and the sheath comprising a first sheath element having a frangible connection to a second sheath element.

10. The medical connector assembly of claim 9, wherein when a second of the single-use connectors connected in series is disconnected from the first of the single-use connectors connected in series, the first sheath element remains disposed about the first of the single-use connectors connected in series and a portion of the multi-use connector and the second sheath element remains disposed about the disconnected second of the single-use connectors connected in series.

11. A medical connector assembly, comprising:
a multi-use connector having a flow control element;
a plurality of single-use connectors releasably connected to each other by a connecting arrangement in series to form a fluid path therethrough;
a sheath disposed over an exterior of the medical connector assembly to extend from the multi-use connector and continuing along the single-use connectors connected in series, and
wherein the multi-use connector is releasably connected to a first of the single-use connectors connected in series, and
wherein the flow control element is configured to prevent fluid flow through the multi-use connector until a sufficient fluid pressure difference across the flow control element is reached;
wherein the sheath comprises a first sheath element having a frangible connection to a second sheath element;
wherein, when a second of the single-use connectors connected in series is disconnected from the first of the single-use connectors connected in series, the first sheath element remains disposed about the first of the single-use connectors connected in series and a portion of the multi-use connector and the second sheath element remains disposed about the disconnected second of the single-use connectors connected in series.

12. The medical connector assembly of claim 11, wherein the flow control element is configured to prevent fluid flow through the multi-use connector when the first of the single-use connectors connected in series is disconnected from the multi-use connector.

13. The medical connector assembly of claim 12, wherein the flow control element is configured to prevent fluid flow in either direction through the multi-use connector.

14. The medical connector assembly of claim 11, wherein the flow control element is a one-way check valve.

15. The medical connector assembly of claim 11, wherein the flow control element is a two-way check valve.

16. The medical connector assembly of claim 11, wherein the flow control element is a slit diaphragm.

17. The medical connector assembly of claim 11, wherein, when the second of the single-use connectors connected in series is disconnected from the first of the single-use connectors connected in series, the first of the single-use connectors connected in series remains connected to the multi-use connector as a sterility retaining cover.

* * * * *

UNITED STATES PATENT AND TRADEMARK OFFICE
CERTIFICATE OF CORRECTION

PATENT NO.         : 10,857,345 B2
APPLICATION NO.    : 15/974764
DATED              : December 8, 2020
INVENTOR(S)        : Uber et al.

Page 1 of 1

It is certified that error appears in the above-identified patent and that said Letters Patent is hereby corrected as shown below:

In the Specification
In Column 20, Line 6, delete "folding elements 224, 226" and insert -- folding elements 234, 236 --, therefor.
In Column 22, Line 62, delete "slot 200" and insert -- slot 1000 --, therefor.

Signed and Sealed this
Ninth Day of February, 2021

Drew Hirshfeld
*Performing the Functions and Duties of the
Under Secretary of Commerce for Intellectual Property and
Director of the United States Patent and Trademark Office*